US005994526A

United States Patent [19]

Meulewaeter et al.

[11] Patent Number: 5,994,526

[45] Date of Patent: Nov. 30, 1999

[54] GENE EXPRESSION IN PLANTS

[75] Inventors: Frank Meulewaeter, Lokeren; Marcus Cornelissen, Heusden; Roel Van Aarssen, Nazareth; Piet Soetaert, Laarne; Veronique Gossele, Ghent, all of Belgium

[73] Assignee: Plant Genetic Systems, Belgium

[21] Appl. No.: 08/880,169

[22] Filed: Jun. 20, 1997

Related U.S. Application Data

[60] Provisional application No. 60/042,915, Jun. 21, 1996.

[51] Int. Cl.[6] .............................. C12N 15/29; C12N 5/04; C12N 15/82; C12N 15/64

[52] U.S. Cl. .................... 536/24.1; 536/23.6; 536/23.71; 435/69.1; 800/287

[58] Field of Search .................................. 536/24.1, 23.6, 536/23.71; 435/69.1; 800/205, DIG. 56

[56] References Cited

U.S. PATENT DOCUMENTS

| | | |
|---|---|---|
| 4,820,639 | 4/1989 | Gehrke . |
| 5,037,745 | 8/1991 | McAllister . |
| 5,102,802 | 4/1992 | McAllister . |
| 5,489,527 | 2/1996 | Wilson . |

FOREIGN PATENT DOCUMENTS

| | | |
|---|---|---|
| 0589110A1 | 3/1994 | European Pat. Off. . |
| 0589841A2 | 3/1994 | European Pat. Off. . |
| 91/00905A1 | 2/1991 | WIPO . |
| 91/16432A1 | 10/1991 | WIPO . |
| 93/09218A1 | 5/1993 | WIPO . |
| 95/24493A1 | 9/1994 | WIPO . |
| 95/24492A1 | 9/1995 | WIPO . |

OTHER PUBLICATIONS

Adang et al., Plant Molecular Biology, 21, 1131–1145 (1993).

Bourque et al., Plant Molecular Biology, 19, 641–647 (1992).

Carozzi et al., Plant Molecular Biology, 20, 539–548 (1992).

Coutts et al., Journal of General Virology, 72, 1521–1529 (1991).

Danthinne et al., Virology, 185, 605–614 (1991).

Danthinne et al., Molecular and Cellular Biology, 13, No. 6, 3340–3349 (1993).

Dunn et al., J. Mol. Biol., 166, 477–535 (1983).

Fischhoff et al., Bio/Technology, 5, 807–813 (1987).

Jackson et al., RNA, 1, 985–1000 (1995).

Joho et al., J. Mol. Biol., 215, 21–29 (1990).

Klement et al., J. Mol. Biol., 215, 21–29 (1990).

Lassner et al., Plant Molecular Biology, 17, 229–234 (1991).

Macdonald et al., J. Mol. Biol., 232, 1030–1047 (1993).

Marshallsay et al., Nucleic Acids Research, 18, No. 12, 3459–3466 (1990).

McBride et al., Bio/Technology, 13, 362–365 (Apr. 1995).

McGraw et al., Nucleic Acids Research, 13, No. 18, 6753–6766 (1985).

McMullen et al., Nucleic Acids Research, 14, No. 12, 4953–4968 (1986).

Meulewaeter et al., Virology, 177, 699–709 (1990).

Meulewaeter et al., Journal of Virology, 66, No. 11, 6419–6428 (Nov. 1992).

Murray et al., Plant Molecular Biology, 16, 1035–1050 (1991).

Perlak et al., Proc. Natl. Acad. Sci. USA, 88, 3323–3328 (Apr. 1991).

Riviere et al., Journal of General Virology, 71, 1887–1896 (1990).

Sengupta et al., J. Biological Chemistry, 264, No. 24, 14246–14255 (Aug. 25, 1989).

Tarun, Jr., Genes & Development, 9, 2997–3007 (1995).

Timmer et al., J. Biological Chemistry, 268, No. 13, 9504–9510 (May 1993).

Vaeck et al., Nature, 328, No. 6125, pp. 33–37 (1987).

Wang et al., J. Biological Chemistry, 270, No. 22, 13446–13452 (Jun. 1995).

Ysebaert et al., J. Mol. Biol., 143, 273–287 (1980).

Napoli et al. The Plant Cell. 1989. vol. 2: 278–289.

Linthorst et al. The Plant Cell. 1989. Mar. issue. vol. 3: 285–291.

Carvalho et al. The EMBO J. 1992. vol. 11: 5995–5602.

Gordon–Kamm et al. The Plant Cell. 1990. vol. 2: 603–618.

Hofte et al. European Journal of Biochemistry. 1986. vol. 161: 273–280.

McBride et al. Bio/Technology. 1995. Apr. issue. vol. 13: 3622–3625.

(List continued on next page.)

*Primary Examiner*—Lynette R. F. Smith

*Assistant Examiner*—Ousama M-Faiz Zaghmout

*Attorney, Agent, or Firm*—Birch, Stewart, Kolasch & Birch, LLP

[57] ABSTRACT

The present invention provides chimeric genes that comprise a first promoter recognized by a DNA-dependent RNA polymerase different from a eukaryotic RNA polymerase II; a DNA region encoding a chimeric RNA which comprises a 5' UTR, an AU-rich heterologous coding sequence, a 3' UTR; and optionally a terminator sequence recognized by said RNA polymerase, wherein the first promoter and the DNA region encoding the chimeric RNA are operably linked such that upon transcription by the RNA polymerase an uncapped RNA species is produced which comprises a first translation enhancing sequence derived from the 5' region of genomic or subgenomic RNA of a positive stranded RNA plant virus; a heterologous RNA coding sequence encoding a polypeptide or protein of interest, preferably from an AT-rich gene; and a second translation enhancing sequence derived from the 3' region of genomic or subgenomic RNA of a positive-stranded RNA plant virus, wherein the uncapped RNA species is capable of being translated in the cytoplasm of a plant cell to produce the protein or polypeptide. Also provided in the invention are plant cells and plants comprising these chimeric genes, integrated in their nuclear DNA, whereby the plant cell produces the RNA polymerases corresponding to the used promoters and terminators. Further the invention provides a process for producing a plant expressing a protein or polypeptide encoded by a heterologous gene which comprises the steps of transforming the nuclear genome of a plant cell with the above-mentioned chimeric genes; and regenerating a transformed plant from the transformed cell.

5 Claims, 2 Drawing Sheets

OTHER PUBLICATIONS

Albert et al. Molecular Biology of the Cell. Book. Second edition. 1989.

Elroy–Stein et al. Proc. Natl. Acad. Sci. 1989. vol. 86: 6126–6130.

McGraw et al. Nucleic Acid Research. 1985. vol. 13: 6753–6766.

Klement et al. Journal of Molecular Biology. vol. 1990. vol. 215: 21–29.

Seurinck and Emmelo, Virology. 1990. Aug. issue. vol. 177: 699–709.

Seurinck et al. Virology. 1991. Dec. issue. vol. 185: 605–614.

Lassner et al. Plant Molecular Biology. 1991. vol. 17: 229–234.

Sengupta et al. Journal of Biological Chemistry. 1989. vol. 264: 14246–14255.

GENE EXPRESSION IN PLANTS

This application claims benefit of Provisional Application Ser. No. 60/042,915 filed Jun. 21, 1996.

FIELD OF THE INVENTION

The invention relates to the efficient expression in plants of AT-rich genes, especially *Bacillus thuringiensis* (Bt) genes encoding insecticidal crystal proteins (ICP). The invention thus relates to a process that comprises the RNA polymerase II independent production of predominantly uncapped, non-polyadenylated RNA transcripts of the native coding sequences of AT-rich genes, preferably Bt ICP genes, said transcripts comprising translation enhancing sequences, particularly those derived from the 5' region and 3' region of positive-stranded RNA plant viruses, preferably of necroviruses, that enable efficient cap- and poly(A)-independent translation of the RNA transcripts in plant cells to yield high levels of proteins specified by the AT-rich genes, more particularly insecticidal levels of Bt ICPs.

BACKGROUND OF THE INVENTION

The recent developments in plant genetic engineering allow routine introduction of recombinant DNA in a wide range of plants. Transcription and translation was observed for most of the chimeric genes, however suboptimal expression is often encountered when expression of AT-rich genes is attempted. One of the prime examples of such difficulties was the expression of Bt ICPs.

Numerous publications teach the expression of different Bt ICPs in a wide range of plant species. Truncating the Bt ICP genes so as to encode a smaller and more soluble protein that retained full toxicity was found to be critical to obtain insect controlling amounts of Bt ICP in the plants [Vaeck et al., *Nature,* 328: 33–37 (1987); Fischhof et al., *Bio/Technology* 5: 807–813 (1987); Carozzi et al., *Plant Molecular Biology* 20: 539–548 (1992)].

Subsequent publications described the enhancement of the expression levels of Bt ICP genes in plant species, in order to be able to target also less susceptible insect species. Different approaches were followed to modify the introduced bacterial DNA sequences encoding Bt ICPs to avoid the presence of sequences that could negatively affect expression in the plant cells. To this end, nucleic acid sequences were provided that encode a Bt ICP with essentially the same amino acid sequence as an existing Bt ICP but wherein one or more of the following modifications were included:

- the nucleic acid sequence surrounding the translation initiation codon was changed to resemble more the translation initiation sequences preferably used by plants.
- the overall codon usage was modified to better reflect the preferred codon usage of a particular plant species.
- cryptic promoter signals were removed.
- nucleic acid sequences that target the hnRNA into an abortive splicing pathway were eliminated.
- potential termination signals for DNA-dependent RNA polymerase II within the coding sequence were removed.
- putative mRNA destabilizing sequences were replaced.
- presumptive alternative polyadenylation sites were avoided.

[Perlak et al., *Proc. Natl. Acad Sci. USA* 88: 3324–3328 (1991); Adang et al., *Plant Mol. Biol.* 21: 1131–1145 (1993), Murray et al. *Plant Mol. Biol.* 116:1035–1050 (1991) WO 91/16432, WO 93/09218].

Recently, Mc Bride et al. described the introduction of a native Bt ICP coding sequence under control of a T7 promoter or a plastid expression signal in the chloroplasts of tobacco plants in an attempt to circumvent the problem of poor expression of full-length protoxin genes from the nucleus of plants, particularly those with a high AT-content. The regenerated plants from these transplastomic lines were reported to express Bt ICP at a high level in mature leaves using the prokaryotic-like transcriptional and translational machinery of the plastid (Mc Bride et al., *Bio/Technology* 13: 362–365 (1995); WO 95/24492, WO 95/24493). However, the transformation process set forth in these references is complicated because it requires the use of plastid transformation vectors and/or the transport of appropriate polymerases from the cytoplasm to the chloroplasts. Furthermore, the references remain silent on the level of ICPs in tissues other than mature leaves, such as root or stem tissue which constitute important targets for pests such as corn root worm (Diabrotica spp), European corn borer (*Ostrinia nubilalis*) or cutworms (e.g., Agrotis spp.).

Unique features of eukaryotic mRNA are the presence of the $m^7G$ cap at its 5' end and a 3' poly(A) tract. Several functions at different stages of gene expression have been attributed to the cap at the 5' end, which is added shortly after transcription elongation has started, including a role in RNA stabilization, splicing, transport and translation. The cap structure supposedly binds to the translation initiation factor eIF-4F, allowing the ribosomal subunits and proper factors to bind and initiate at the first AUG codon in a favourable sequence context. Absence of this 5' cap structure in naturally capped plant viral RNA or cellular mRNA decreases the translational efficiency substantially [Fletcher et al., *J. Biol. Chem.* 265: 19582–19587 (1990)].

A role for the poly(A) tail found at the 3' end of most eukaryotic mRNAs has been implied in mRNA stability, its transport into the cytoplasm, and its efficient translation [Jackson and Standart, Cell, 62: 15–24,1990]. The poly(A) tail, complexed with poly(A)-binding protein is believed to enhance the formation of 40S translational initiation complexes, presumably through promoting some sort of interaction between 5' and 3'-proximal elements of the mRNA [Tarum and Sachs, *Genes and Dev.* 9: 2997–3007 (1995)].

Whereas the majority of eukaryotic mRNAs have capped 5' ends and poly(A) tails at the 3' ends, the genomic or subgenomic RNAs of plant viruses often lack one or both. For positive-strand RNA viruses, the RNAs are translated early upon infection, even though cellular templates are prevalent. It is often due to the presence of alternative terminal structures that viral RNA templates exhibit high translational efficiency.

U.S. Pat. No. 4,820,639 describes a process and means for increasing production of protein translated from eukaryotic messenger ribonucleic acid comprising transferring a regulatory nucleotide (nt) sequence from a viral coat protein mRNA to the 5' terminus of a gene or complementary deoxyribonucleic acid (cDNA) encoding the protein to be produced to form a chimeric DNA sequence.

U.S. Pat. No. 5,489,527 and the European patent publication (EP) 0270611 both describe the use of 5' regions of RNA viruses as enhancers of translation of mRNA, especially 5' regions derived from plant RNA viruses.

Publication of the PCT patent application (WO) 91/00905 and U.S. Pat. No. 5,135,855 describe the use of untranslated regions from an encephalomyocarditis virus to confer cap-independent translation to RNAs in mammalian cells, particularly when a prokaryotic transcription system is used in these eukaryotic cells.

EP 0589841 provides a dual method for producing male-sterile plants, as well as compositions and methods for high level expression of a coding region of interest in a plant by expression of a T7 RNA polymerase in a plant cell that contains a second expression cassette comprising a T7 5' regulatory region linked to the coding region of interest.

SUMMARY

In accordance with the invention chimeric genes are provided that comprise:

a.) a first promoter recognized by a DNA-dependent RNA polymerase different from a eukaryotic RNA polymerase II, particularly a T3 or T7 RNA polymerase specific promoter;

b.) a DNA region encoding a chimeric RNA which comprises a 5' UTR, a heterologous coding sequence, preferably an AU-rich coding sequence, and a 3' UTR; and optionally c.) a terminator sequence recognized by said RNA polymerase wherein the chimeric RNA, produced by the RNA polymerase, is uncapped and comprises:

i) a first translation enhancing sequence derived from the 5' region of genomic or subgenomic RNA of a positive stranded RNA plant virus, preferably a necrovirus, especially STNV-2 or TNV-A, located in the 5' region of the chimeric RNA;

ii) a second translation enhancing sequence derived from the 3' region of genomic or subgenomic RNA of a positive-stranded RNA plant virus, preferably a necrovirus, especially STNV-2 or TNV-A, located in the 3' region of the chimeric RNA;

and which is capable of being translated in the cytoplasm of a plant cell, to produce the protein or polypeptide. The transcribed uncapped RNA coding sequence may be polycistronic.

Also provided in the invention are plant cells and plants, particularly corn plant cells and plants, comprising these chimeric genes, integrated in their nuclear DNA, whereby the plant cell produces the RNA polymerases corresponding to the used promoters and terminators.

More particularly, it is a further objective of the invention to provide plant cells and plants, comprising these chimeric genes, integrated in their nuclear DNA, wherein the first promoter is a single subunit bacteriophage RNA polymerase specific promoter, such as a T3 or T7 RNA polymerase specific promoter, and wherein such plant cells or plants further comprise a chimeric polymerase gene including:

a.) a second plant-expressible promoter;

b.) a DNA sequence encoding a single subunit bacteriophage RNA polymerase such as a T3 or T7 RNA polymerase functionally linked to a nuclear localization signal;

operably linked so that upon expression of the chimeric polymerase gene a functional and properly located RNA polymerase is produced.

The invention further provides a process for producing a plant expressing a protein or polypeptide encoded by a heterologous gene, preferably an AT-rich gene, especially a Bt ICP encoding gene, which comprises the steps of:

a.) transforming the nuclear genome of a plant cell with the above-mentioned chimeric genes; and b.) regenerating a transformed plant from the transformed cell.

DETAILED DESCRIPTION OF INVENTION

Figure 1A:
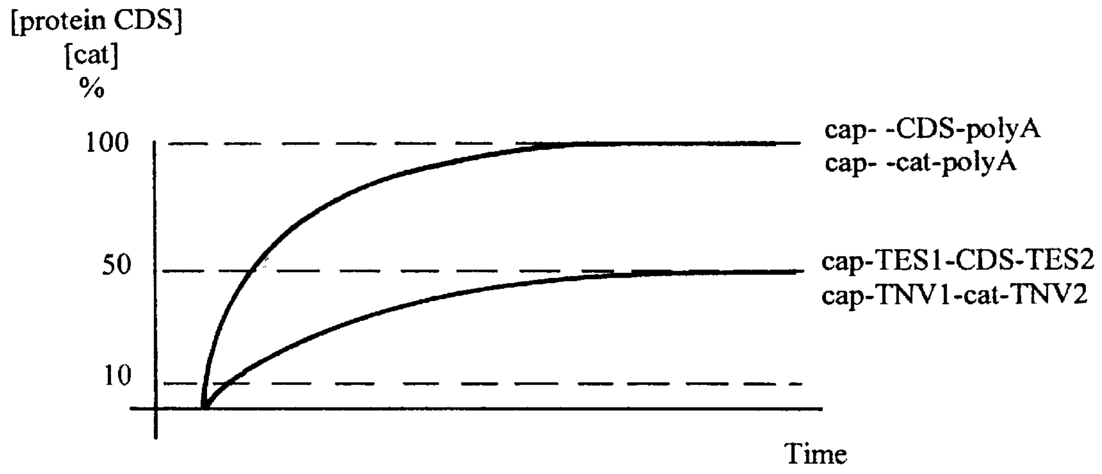
FIG. 1A schematically represents the relative protein accumulation profiles in plant protoplasts obtained by translation of a capped chimeric RNA comprising the translation enhancing sequences of the invention, in reference to an efficiently translated capped and polyadenylated RNA.

The difficulties associated with the expression of Bt ICP genes in plant cells are also often encountered when expressing other heterologous genes with high AT-content. AT-rich genes have an enhanced probability of harbouring cryptic signals interfering with efficient transcription and translation in plant cells, especially in monocotyledonous cells, such as corn cells. Expression problems are magnified when the AT content of the coding region of the heterologous gene surpasses significantly the mean AT content of the coding regions of the host plant in which expression is attempted. These expression problems might already arise when the coding sequence of the gene of interest, although not particularly AT-rich when taken as a whole, contains an AT-rich nucleotide-stretch of about 400 residues.

Accordingly, it was a main object of the present invention to provide a reliable method for efficient expression in plant cells of AT-rich genes, particularly Bt ICP genes without having to rely on expensive, labourious and time-consuming methods to implement the various approaches that have been described.

The present invention provides a new method to promote expression to a high level, of coding sequences, preferably coding sequences of AT-rich genes such as Bt ICP genes, particularly native coding sequences of Bt ICP genes which are integrated in the plant's nuclear genome. It was realized that problems associated with the expression of coding sequences of heterologous AT-rich genes at the transcriptional and/or post-transcriptional level can be overcome by using an RNA polymerase different from the eukaryotic DNA-dependent RNA polymerase II, to produce uncapped RNAs encoding the protein or polypeptide of interest. These uncapped RNAs are then efficiently translated into the desired protein or polypeptide, by using the translation enhancing sequences provided in this invention.

The invention is based on the realization that transciption by an RNA polymerase different from the eukaryotic DNA dependent RNA polymerase II, of AT-rich genes such as Bt ICP genes, particularly native coding sequences of Bt ICP genes, integrated in the nuclear genome of a plant, generates sufficiently large amounts of RNA, without suffering from the mentioned transcriptional and post-transcriptional problems. The resulting RNA is however uncapped and non-polyadenylated.

The invention is further based on the finding by the applicants, that when uncapped RNAs comprising native coding sequences of heterologous genes and suitable translation enhancing sequences derived from 5' and 3' regions of the genomic RNA coding for the coat protein of a necrovirus, such as STNV-2, are introduced in plant cells, these RNAs are translated efficiently.

The invention thus provides the means and methods to transcribe AT rich genes by an RNA polymerase different from the eukaryotic DNA dependent RNA polymerase II, to produce uncapped RNAs encoding the protein or polypeptide of interest, which are efficiently translated by the inclusion of translation enhancing sequences from 5' and 3' regions of RNA viruses which allow efficient translation of uncapped RNAs in a cap-independent manner. To this end, cap-independently expressed chimeric genes are provided comprising an AT-rich coding sequence and DNA encoding translation enhancing sequences of a necrovirus, under control of a promoter recognized by an RNA polymerase different from eukaryotic RNA polymerase II. Integration of such chimeric genes in a plant cell expressing the alternative RNA polymerase results in the production of predominantly uncapped and non-polyadenylated RNA transcripts which are translated efficiently due to the presence of the translation enhancing sequences.

As used herein, both “leader” and “5'UTR” refer to the part of a protein-encoding RNA molecule, preceding the initiation codon of the coding sequence. These terms are employed interchangeably and may also be used to refer to a DNA, encoding such a leader. Similarly, “trailer” and “3'UTR” refer to the part of a protein-encoding RNA molecule, downstream of the stop codon of the coding sequences. Again, these terms are employed interchangeably and may also be used to refer to a DNA encoding such a trailer. Generally, but not exclusively, the 5'UTR and 3'UTR of an RNA plant virus mentioned in this specification flank the coding sequence of the coat protein of that virus.

As defined herein, the “5' region” of a protein-encoding RNA molecule, refers to the extreme 5' end of that RNA and comprises at least the 5'UTR of that RNA but may include several nucleotides extending immediately downstream of the initiation codon of the homologous coding region. Similarly, the “3' region” of a protein-encoding RNA molecule, refers to the extreme 3' end of that RNA and comprises at least the 3'UTR of that RNA but may include several nucleotides extending immediately upstream of the stop codon of the homologous coding region.

As used herein “coding region” or “coding sequence” refers to an RNA molecule or sequence which can be translated into a continuous sequence of amino acids of a biologically active protein or peptide (e.g., an enzyme or a protein toxic to insects) or to the DNA molecule or sequence encoding such an RNA. Whether the “coding region” refers to a RNA or DNA molecule will be readily understood by the context. A coding sequence to be utilized in a cap-independently expressed chimeric gene will be generally derived from the coding region of a heterologous gene, and an appropriate initiation codon has to be provided, if necessary.

A “DNA region encoding an RNA region” may refer to any part of a DNA molecule that is transcribed and thus can relate to the entire transcribed region of a gene, but also to parts thereof, e.g., part of a coding sequence, a DNA-region corresponding to a first or second translation enhancing sequence, a 5' or 3' UTR, or a 5' or 3' region.

Whenever cited in this application, “expression” of a gene refers at least to the combination of phenomena (transcriptional, post-transcriptional and translational events) which result in the production of the primary translation product, i.e., a protein or a polypeptide. However, in some instances it will be clear that the term also relates to the effect the translation product or its derivative may have on the phenotype of the cell or of the plant.

A cap-independently-expressed chimeric gene (CIG) of this invention generally comprises:

a) a first promoter recognized by a DNA-dependent RNA polymerase, different from eukaryotic DNA-dependent RNA polymerase II,
b) a DNA encoding an RNA molecule which comprises:
    1) an untranslated leader sequence;
    2) a coding region encoding a heterologous protein or polypeptide, preferably an AU-rich coding region; and
    3) an untranslated trailer sequence, and, optionally,
c) a terminator sequence recognized by the same RNA polymerase which recognizes the first promoter.

These elements are provided as operably linked components in the 5' to 3' direction.

The CIGs of this invention are further characterized in that they comprise DNAs encoding first and second translation enhancing sequences.

In the uncapped RNA that is encoded by the CIG, the first translation enhancing sequence is generally located in the untranslated leader sequence, but it may overlap with the coding region, i.e., it may extend downstream of the initiation codon of the coding region. Preferably, the first translation enhancing sequence is located around that translation initiation codon.

In the RNA that is encoded by the CIG, the second translation enhancing sequence is generally located in the untranslated trailer sequence, but it may also overlap with the coding region, i.e., it may extend upstream of the stop codon of the coding region. Preferably, the second translation enhancing sequence is located around that stop codon.

Preferred cap-independently expressed chimeric genes of the invention are CIGs as described above, wherein the DNA encoding a heterologous protein or polypeptide is AT-rich. “AT-rich” DNA coding sequences as referred to herein, are those coding DNA sequences, comprising a continuous nucleotide sequence of at least 400 nucleotides, preferably of a least 600 nucleotides in length, with an AT content of at least 55%, preferably of at least 57.5%, particularly of at least 60%, more particularly of at least 62%. It goes without saying that “AT rich” coding sequences also include those coding sequences, where the entire coding sequence has an AT content of at least 55%, preferably of at least 57.5%, particularly of at least 60%, especially of at least 62%. Evidently, coding sequences smaller than 400 nucleotides are considered AT-rich when the entire coding sequence has an AT content of at least 55%, preferably of at least 57.5%, particularly of at least 60%, especially of at least 62%. AT rich coding sequences thus include but are not limited to e.g., coding sequences of Bt ICP genes, but also sequences encoding fusion proteins between an Bt ICP and a protein encoded by a GC-rich coding sequence. It is clear, that a coding RNA sequence referred to as “AU rich” is defined by the same criteria as an “AT rich DNA”, except that thymine (T) is replaced by uracil (U).

Another class of preferred CIGs are those CIGs wherein the first and second translation enhancing sequences are derived from a TNV strain, particularly from TNV-A, especially from TNV sg RNA 2.

In accordance with the invention, the CIGs are integrated in the nuclear genome of cells of a host plant. In order to transcribe the CIGs independently from the host-encoded RNA polymerase II, so as to produce predominantly uncapped, non-polyadenylated RNA transcripts, these genes contain promoters recognized by the endogenous RNA polymerase I or III of the host, or recognized by a bacteriophage single subunit RNA polymerase. In the latter case, the gene encoding the single subunit RNA polymerase is also introduced and expressed in a functional and properly located form in the same plant cell. It goes without saying that the choice of the RNA polymerase will depend on the particular promoter of the CIG and vice versa.

As used herein, the term "heterologous" with regard to a coding sequence refers to any coding sequence which is different from the coding sequence naturally associated with a 5' UTR or 3' UTR from a viral RNA from which the first or second translation enhancing sequences are derived. Preferably a heterologous coding region does not contain a region of more than 20, preferably not more than 15 codons of the viral RNA ccoding region. "Homologous" on the contrary means that such a coding sequence is naturally associated with a 5' UTR or 3' UTR from a viral RNA from which the first or second translation enhancing sequences are derived.

A heterologous, respectively homologous protein is thus a protein encoded by a heterologous, respectively homologous coding sequence.

As used herein, the term "necrovirus" refers to any plant virus isolate normally included in this taxonomic group, as well as their satellite viruses, exemplified by, but not limited to, tobacco necrosis virus strains, satellite tobacco necrosis virus strains, chenopodium necrosis virus, carnation yellow stripe virus, and lisianthus necrosis virus.

As used herein, the term "native DNA" or "native DNA sequence" refers to a DNA as found in its natural state, as well as a DNA containing small modifications whereby the overall AT content of that DNA is essentially retained, and the amount of modified bases, preferably of modified adenine or thymine, is limited to maximally 3%, particularly less than 1%. A native DNA with small modifications should have at least 95%, preferably 99% sequence identity with respect to that native DNA without such modifications. Examples of such modifications include, but are not limited to, the modification of the nucleotide sequence to introduce or remove a restriction enzyme recognition site or to change one or more amino acids in order to make a protein protease-resistant. For the purpose of the invention, the term native DNA will be used predominantly with regard to all or part of the heterologous coding sequence encoding a biologically functional protein or polypeptide, such as a BT ICP coding region. In this regard, the native Bt ICP encoding sequence may thus be a truncated version comprising the minimal toxic fragment.

"Viral RNA" as used herein designates any genomic or subgenomic RNA of, or produced by a positive stranded RNA plant virus in nature.

This invention makes use of an RNA polymerase that generates uncapped, non-polyadenylated RNA transcripts of a CIG. The nature of the RNA polymerase evidently determines the first promoter to be included in the CIG and vice versa.

A useful RNA polymerase is a bacteriophage single subunit RNA polymerase such as the RNA polymerases derived from the *E. coli* phages T7, T3, ϕI, ϕII, W31, H, Y, A1, 122, cro, C21, C22, and C2; *Pseudomonas putida* phage gh-1; *Salmonella typhimurium* phage SP6; *Serratia marcescens* phage IV; Citrobacter phage ViIII; and Klebsiella phage No.11 [Hausmann, *Current Topics in Microbiology and Immunology,* 75: 77–109 (1976); Korsten et al., *J. Gen Virol.* 43: 57–73 (1975); Dunn et al., *Nature New Biology,* 230: 94–96 (1971); Towle et al., *J. Biol. Chem.* 250: 1723–1733 (1975); Butler and Chamberlin, *J. Biol. Chem.,* 257: 5772–5778 (1982)]. Especially preferred are the T3 RNA polymerase and the T7 RNA polymerase. Obviously, when these RNA polymerases are used the first promoter should be a T3 RNA polymerase specific promoter and a T7 RNA polymerase specific promoter, respectively. For the sake of convenience, a T3 RNA polymerase specific promoter and a T7 RNA polymerase specific promoter are referred to as a T3 promoter and a T7 promoter, respectively. A T3 promoter to be used as a first promoter in the CIG can be any promoter of the T3 genes as described by McGraw et al, *Nucl. Acid Res.* 13: 6753–6766 (1985). Alternatively, a T3 promoter may be a T7 promoter which is modified at nucleotide positions -10, -11 and -12 in order to be recognized by T3 RNA polymerase [(Klement et al., *J. Mol. Biol.* 215, 21–29(1990)]. A preferred T3 promoter is the promoter having the "consensus" sequence for a T3 promoter, as described in U.S. Pat. No. 5,037,745.

A T7 promoter which may be used according to the invention, in combination with T7 RNA polymerase, comprises a promoter of one of the T7 genes as described by Dunn and Studier, *J. Mol. Biol.* 166: 477–535 (1983). A preferred T7 promoter is the promoter having the "consensus" sequence for a 17 promoter, as described by Dunn and Studier (supra).

It should be noted that T3 or 17 promoters as described above include nucleotides immediately downstream of the transcription initiation site. At the 3' end of the described T3 or 17 promoter for use in this invention, up to six nucleotides can be removed to prevent the incorporation of additional nucleotides in the 5' UTR of the transcripts from the CIGs. Particularly preferred are the T3 promoter of SEQ ID No.18 between the nucleotide positions 14 and 32 and the T7 promoter of SEQ ID No.30 between nucleotide positions 22 and 39. Another particularly preferred promoter is the 17 promoter of SEQ ID No. 30 between nucleotide positions 22 and 39 followed by 4 nucleotides of the consensus sequence (i.e., GGAG) as described by Dunn and Studier (supra).

Another useful RNA polymerase for application in this invention is RNA polymerase I. Accordingly, the CIG of this invention may comprise a RNA polymerase I promoter. RNA polymerase I normally transcribes the tandemly repeated rRNA genes in eukaryotic cells such as plant cells, and the promoter signals are located in the intergenic spacer sequences between the rRNA gene repeats. It is preferred that the RNA polymerase I promoter used in the CIG of this invention originates or is derived from the plant species to be transformed with the CIG, although this is not required.

In a preferred embodiment, a functional RNA polymerase I specific rRNA promoter region from corn derived from the 3 kb intergenic spacer as described for Black Mexican Sweet Maize [McMullen et al., *Nucl. Acids Res.* 14: 49534968 (1986)] is used. A preferred promoter region comprises the nucleotide sequence of the EMBL nucleotide sequence database under accession number X03990 (EMBL X03990, which is herein incorporated by reference) between nucleotide positions 2160 and 2296, particularly a promoter region including all subrepeats of the intergenic spacer, such as a promoter region comprising the nucleotide sequence of EMBL X03990 between nucleotide positions 154 and 3118. Especially preferred is a promoter region wherein some of the subrepeats have been deleted, such as a promoter region comprising the nucleotide sequence of EMBL X03990 between nucleotide positions 939 and 3118. More particularly preferred are promoter regions wherein some or all of the nucleotides downstream of the transcription initiation point have been deleted such as a promoter region comprising the nucleotide sequence of EMBL X03990 between nucleotide positions 154 and 2590 or a promoter region comprising the nucleotide sequence of EMBL X03990 between nucleotide positions 2160 and 2296. It is clear that for the purpose of the invention corresponding promoter regions from another isolated rRNA intergenic repeat from the same maize variety can be used, or from an isolated rRNA intergenic repeat from another maize variety e.g., A619 [Toloczyki and *Feix, Nucl. Acids Res* 14:4969–4986 (1986); EMBL Accession No X03989, incorporated herein by reference] is used. Particularly preferred are the corresponding RNA polymerase I promoter regions derived from the 3 kb intergenic region of the maize line B73.

Other rRNA intergenic spacers, comprising RNA polymerase I promoters which may be used according to the invention, are known in the art for rye [Appels et al, *Can J Genet Cytol* 28:673–685 (1986)], wheat [Barker et al, *J. Mol. Biol.* 201: 1–17 (1988)], radish [Delcasso-Tremousaygue et al., *Eur. J. Biochem* 172: 767–776 (1988)], rice [Takaiwa et al., *Plant Mol. Biol.* 15: 933–935(1990)], mung bean [Gerstner et al, *Genome* 30: 723–733 (1988), Schiebel et al., *Mol Gen Genet* 218: 302–307 (1989)], potato [Borisjuk and Hemleben, *Plant Mol Biol.* 21; 381–384 (1993)], tomato [Schmidt-Puchta et al., *Plant Mol Biol* 13: 251–253 (1989)], Vicia faba [Kato et al, *Plant Mol. Biol.* 14: 983–993 (1990)], *Pisum sativum* [Kato et al., supra (1990)] and *Hordeum bulbosum* [Procunier et al., *Plant Mol Biol.* 15: 661–663 (1990)].

Yet another useful RNA polymerase for application in this invention is RNA polymerase III. Accordingly, the cap-independently expressed chimeric gene of this invention may comprise a RNA polymerase III promoter. RNA polymerase III normally transcribes the majority of small RNAs, such as tRNAs, 5S RNAs and small nuclear RNAs (snRNAs) involved in mRNA processing, in eukaryotic cells such as plant cells. Suitable promoters for this invention recognized by RNA polymerase III are the promoters transcribing snRNAs of plants such as U3 or U6 snRNA from *Arabidopsis thaliana* [Waibel and Filipowicz, *Nucl. Acids Res.* 18: 3451–3458 (1990), Marshallsay et al., *Nucl. Acids Res.* 18: 3459–3466 (1990)1 or the promoter transcribing tRNAs of plants such as $tRNA^{met}$ from soybean [Bourque and Folk, *Plant Mol. Biol.* 19: 641–647(1992)].

According to the invention, the transcribed region of a CIG, comprises a heterologous AT-rich coding sequence, as defined above. In a preferred embodiment of the invention the transcribed region comprises a sequence encoding a Bt ICP having insecticidal activity to at least one insect species. Especially preferred is a transcribed region comprising a sequence encoding a truncated Bt ICP, which lacks nucleotides either at the 5' end or the 3' end of the coding sequence, or both, but still comprises the sequence coding for the minimal toxic fragment. Particularly preferred Bt ICP encoding sequences for use in this invention are cry1Ab5, cry9C, cry1Ba, cry3C, cry3A, cry1Da and cry1Ea. As used herein, cry1Ab5 represents the cry1Ab gene described by H öfte et al, *Eur. J. Biochem.* 161: 273–280 (1986); cry9C represents the cry1H gene described by Lambert et al., *Appl. and Env. Microbiol.* 62: 80–86 (1996); cry1Ba represents the cry1B described by Brizzard and Whitely, *Nucl. Acid Resarch* 16: 4168–4169 (1988); cry3C represents the cryIIID gene described by Lambert et al., *Gene* 110: 131–132 (1992); cry3A represents the cryIIIA gene described by Höfte et al., *Nuc. Acids Res.* 15: 7183; cry1Da and cry1Ea represent the bt4 and bt18 genes, respectively, described in WO 90/02801, according to the classification proposed by Crickmore et al, Abstract presented at the 28th annual meeting of the Society for Invertebrate Pathology, Jul. 16–21, 1995. CIGs of the invention may further include the use of genes encoding a Bt ICP fused to a protein allowing selection, e.g., gentamycin acetyl transferase (GAT) encoded by aac(6') or phosphinotricin acetyl transferase (PAT) encoded by bar. CIGs encoding chimeric toxins, wherein a domain of the toxic BT ICP fragment has been exchanged for a similar domain of another BT ICP, as described by Bosch et al. [BIO/TECHNOLOGY 12, 915–918(1994)] are also encompassed by the invention.

The CIGs according to the invention may be polycistronic, comprising between the first and second translation enhancing sequence at least 2 and up to 5 cistrons, although more cistrons may be possible. Transcription of such a polycistronic CIG yields polycistronic RNA that should preferably comprise an internal ribosome entry site [Jackson and Kaminski, *RNA* 1: 985–1000 (1995); Levis and Astier-Monifacier, *Virus Genes* 7: 367–379 (1993); Basso et al. *J. Gen. Virology* 75: 3157–3165 (1994)] between the cistrons. For the purpose of this invention it is preferred that at least one cistron is AT-rich.

The CIGs used in the invention may further include a terminator recognized by the RNA polymerase which is used to enable transcription of the CIG. Suitable terminators are known in the art and should preferably be chosen according to the specific promoter that is used. For instance, when a T3 promoter is used, a T3 specific terminator such as described by Sengupta et al., *J. Biol. Chem.* 264: 14246–14255 (1989), preferably in a duplicated form, can be used. Since a T7 RNA polymerase terminates as efficiently on a T3 terminator (T3-Tϕ) as on a T7 terminator (T7-Tϕ) [Macdonald et al., *J. Mol. Biol.* 232: 1030–1047 (1993)], a terminator region comprising T3-Tϕ may be used as well for CIGs containing a T3 promoter as for those containing a T7 promoter.

Alternatively when promoters specifically recognized by RNA polymerase I are used, the terminator regions used should comprise the corresponding species-specific RNA polymerase I terminators which are present in the intergenic regions between the rRNA repeats [Reeder and Lang, *Molecular Microbiology* 12: 11–15 (1994)].

When promoters specifically recognized by RNA polymerase III are used, the terminator regions used may comprise the corresponding trailer sequences associated with genes normally transcribed by RNA polymerase III, such as the genes encoding U3 or U6 snRNA from *Arabidopsis thaliana* [Waibel and Filipowicz, supra, Marshallsay et al. supra] or the gene encoding $tRNA^{met}$ from soybean [Bourque and Folk, supra].

According to the invention, the CIG integrated in the nuclear genome of a plant cell, is transcribed in an RNA polymerase II independent manner. This can be achieved in accordance with the invention by incorporating in the CIG a promoter and terminator as described above. Whenever the transgenic plant cells do not naturally contain the RNA polymerase required for the recognition of the promoter and transcription of the CIG, these cells need to comprise a second chimeric gene encoding that RNA polymerase, further referred to as the chimeric polymerase gene. When promoters recognized by single subunit RNA polymerases of bacteriophages (e.g., T7 or T3 promoters) are used, a chimeric polymerase gene encoding a T7 or T3 RNA polymerase [U.S. Pat. No. 5,102,802] should also be incorporated in the nuclear DNA of the host plant cell. Further, mutant bacteriophage RNA polymerases as exemplified for T7 RNA polymerase by McDonalds et al., *J. Mol. Biol.* 238:

145–148 (1994), may be used in this invention. Such mutant bacteriophage T7 RNA polymerases no longer recognize the rare termination signals encountered in heterologous genes under control of a T7 promoter, while still terminating at bona fide T7 RNA polymerase termination signals. Also, hybrid bacteriophage RNA polymerases as described by Joho et al., *J. Mol. Biol.* 215: 31–39 (1990), with altered specificity and promoter preference, may be used according to the invention.

Methods to express such bacteriophage RNA polymerases in plant cells, in a functional and properly located form have been described [Lassner et al, *Plant Mol Biol,* 17: 229–234 (1991), EP 0589841]. The chimeric polymerase gene comprises a 5' regulatory region, i.e. the promoter region, necessary for expression in plant cells. This plant-expressible promoter may be a constitutive promoter, such as a CaMV35S promoter [Odell et al. Nature 313, 810–812] or may be regulated in a tissue-specific way, such as the promoters disclosed in WO 92/13957, WO 92/13956 or EP 0344029. Another suitable regulated promoter is a light-inducible promoter such as the promoter of the small subunit of Rubisco. The expression of the single subunit bacteriophage RNA polymerase may also be temporarily regulated using promoters which are only expressed at a certain developmental state, or are induced by external stimuli such as nematode-feeding (WO 92/215757), or fungus-infection (WO 93/19188). Further suitable promoters are plant-expressible promoters regulated by the presence of plant-growth regulators such as abscisic acid, steroid-inducible promoters or copper-inducible promoters.

The spatial or temporal regulation of the promoter used in the chimeric polymerase gene will of course be reflected in the expression pattern of the single subunit bacteriophage RNA polymerase in the transformed plants of this invention, and ultimately in the expression pattern of the CIG comprising the corresponding promoter.

In order to be expressed in a properly located form according to the invention, the single subunit bacteriophage RNA polymerase should be operably linked to a nuclear localization signal (NLS) [Raikhel, *Plant Physiol.* 100: 1627–1632 (1992) and references therein], such as the NLS of SV40 large T-antigen [Kalderon et al. Cell 39: 499–509 (1984)]. It is known that the NLS can be operably linked to the polymerase in different ways. Preferably, the NLS is joined to the amino-terminus of the polymerase, or located within the N-terminal region of the polymerase, particularly within the first 20 amino acids of the polymerase, more particularly between amino acid 10 and 11 of the T7 polymerase.

The chimeric polymerase gene may further include any other necessary regulatory sequences such as terminators [Guerineau et al, *Mol. Gen. Genet.* 226:141–144 (1991), Proudfoot *Cell,* 64:671–674 (1991), Safacon et al., *Genes Dev* 5: 141–149 (1991); Mogen et al., *Plant Cell,* 2: 1261–1272 (1990); Munroe et al., *Gene,* 91: 151–158 (1990); Ballas et al., *Nucleic Acids Research* 17: 7891–7903 (1989); Joshi et al., *Nucleic Acid Research* 15: 9627–9639 (1987)], plant translation initiation consensus sequences [Joshi, *Nucleic Acids Research* 15: 6643–6653 (1987)], introns (Luehrsen and Walbot, *Mol. Gen. Genet.* 225: 81–93 (1991)] and the like, operably linked to the nucleotide sequence of the chimeric polymerase gene.

According to the invention the first and second translation enhancing sequences which may be used are preferably derived from positive-stranded RNA viruses. Preferred translation enhancing sequences are derived from necroviruses, preferably from STNV or TNV strains, especially from STNV-2 or TNV-A sgRNA2.

Figure 1B:
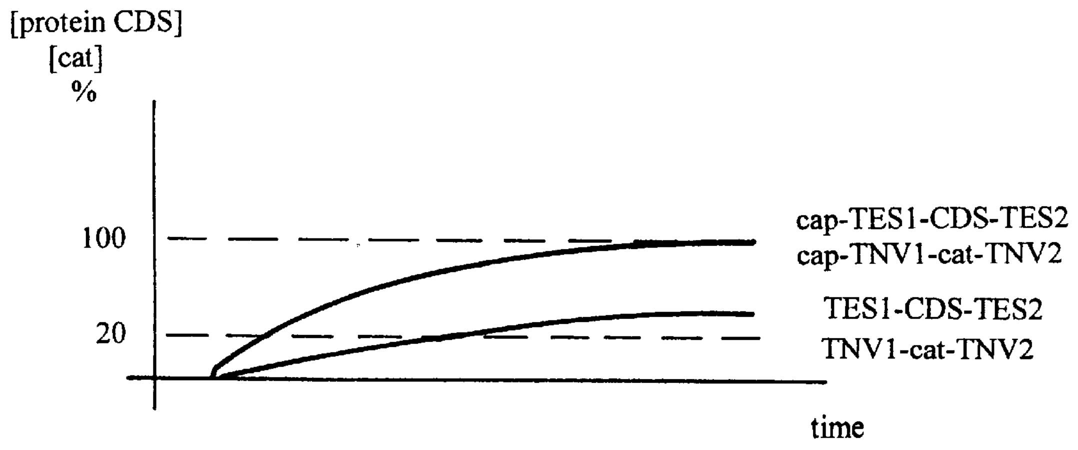
FIG. 1B schematically represents the relative protein accumulation profiles in plant protoplasts obtained by translation of a uncapped chimeric RNA comprising the translation enhancing sequences of the invention, in reference to the capped version of the same chimeric RNA comprising the translation enhancing sequences of the invention.

A first translation enhancing sequence, derived from a 5' region of a viral RNA, predominantly contains sequences of the 5' UTR of that viral RNA and is comprised within the 5' region of the CIG; similarly, a second translation enhancing sequence, derived from a 3' region of a viral RNA, predominantly contains sequences of the 3' UTR of that RNA and is comprised within the 3' region of the CIG. For the purpose of the invention suitable first and second translation enhancing sequences for use in an uncapped RNA of this invention are those combinations which, operably contained within such an uncapped RNA encoding a protein, allow the uncapped, non-polyadenylated RNA of this invention to be translated in plant protoplasts, to a peak level [$P(\infty)=A. t½/In2$; see end of this section for the mathematical formula allowing estimation of functional half-life of the RNA ($t_{1/2}$) and translation efficiency (A)] of the mentioned protein of at least 20%, preferably at least 25%, of the peak level resulting from in vivo translation of similar capped, non-polyadenylated first reference RNA (i.e., a first reference RNA identical to the uncapped RNA but with a cap-structure). The peak level resulting from in vivo translation of the capped non-polyadenylated first reference RNA should be at least 10% of the peak level resulting from in vivo translation of a second reference RNA which is capped and polyadenylated and comprises the Ω leader of TMV [Gallie et al. *Nucl. Acids Res.* 15: 8693–8711(1987)], a coding sequence encoding essentially the same protein as the first reference RNA, preferably the same protein as used in the first reference RNA, and a poly(A) tail comprising around 100 A-residues, such a second reference RNA being extremely efficiently translated. Schematic relative protein-protein profile are represented in FIGS. 1A and 1B; the percentages indicated are those obtained for RNAs comprising TNV sgRNA2 derived translation enhancing sequences. For practical purposes, determination of peak levels can be substituted by determination of protein steady-state levels, the latter being determined after a sufficient long time (e.g., 5 hours for a cat-RNA) after RNA introduction in the protoplasts.

Methods to generate capped and uncapped RNAs in vitro, for the introduction of such RNAs in plant protoplasts and to compare the translation efficiencies and functional half-lives of RNAs are described at the end of this section, as well as in Examples 2, 3 and 4.

Figure 2A:
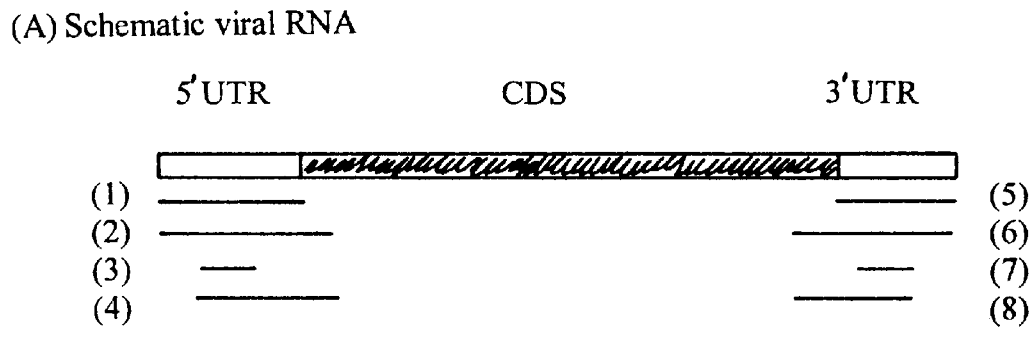
FIG. 2A depicts schematically different possible locations of first and second translation enhancing sequences with regard to the homologous coding sequence and untranslated regions of a viral genomic or subgenomic RNA.

The translation enhancing sequences are largely derived from sequences comprised in the leaders and trailers of genomic or subgenomic viral RNAs (e.g., FIG. 2A (1), (5), (3) and (7). However, for optimal enhancing of cap-independent translation in vivo, it may be necessary to use a first translation enhancing sequence comprising nucleotide sequences extending immediately downstream of the initiation codon of the homologous protein (i.e., comprising nucleotides of the 5' end of the viral homologous coding sequence; e.g., FIG. 2A (2) and (4)), or to use a second translation enhancing sequence comprising nucleotide sequences extending immediately upstream of the stop codon of the homologous protein (i.e., comprising nucleotides of the 3' end of the viral homologous coding sequence; e.g. FIG. 2A (6) and (8)).

On the other hand, in several instances, parts only of the natural 5'UTR or 3'UTR or derivatives thereof (see below) are suitable to provide translational enhancement (e.g., FIG. 2B (3) and (7))

FIG. 2A schematically summarizes the different possible positions of nucleotide sequences comprising translation enhancing sequences (indicated by the thin lines ) with reference to the homologous coding sequence (CDS; indicated as a solid black bar) and 5' and 3' untranslated region (5'UTR and 3'UTR; indicated as open bars) of a viral genomic or subgenomic RNA. First translation enhancing sequences include those indicated by 1–4, second translation enhancing sequences include those indicated by 5–8.

Satellite tobacco necrosis virus (STNV) and tobacco necrosis virus (TNV) are plant viruses belonging to the necrovirus group. STNV is a satellite virus, that relies upon the viral RNA replicase of the helper virus (TNV) for its replication, but codes for its own coat protein (CP). The genome consists of one single-stranded RNA strand with positive polarity, and the nucleotide sequence is known for several strains. Generally, the nucleotide sequence consists of a leader sequence or 5' untranslated region ("UTR") of 29–32 nucleotides (nt), a CP encoding region of 588–597 nt, and a trailer sequence or 3' UTR of 616–622 nt [Ysenbaert et al. *J. Mol. Biol.* 143: 273–287 (1980), Danthinne et al., *Virology* 185, 605–614 (1991)]. The 5' UTRs of the STNV strains are nearly identical and can fold into a hairpin structure with a stem of 6 or 7 bp enclosing a loop of seven residues. The trailer sequences, which exhibit 64% sequence identity between the nucleotide sequence of STNV-1 and STNV-2, can fold into a secondary structure consisting of three (or four) pseudo knots flanked by two hairpins, ending with an extended double helix that spans the last 350 residues of the sequence and includes several internal loops, bulged out nucleotides, and bifurcations. [Danthinne et al, (1991) supra].

The STNV RNA does not contain a $m^7G$ cap structure, nor a covalently linked virus-encoded protein at the 5' end. Neither does it contain a poly(A) tail at the 3' end [Horst et al. Biochemistry 10: 4748–4752 (1971); Smith and Clark, *Biochemistry* 18: 1366–1371(1976)]. Yet, STNV RNA is translated efficiently in vitro. Mutations and deletions in the STNV RNA, followed by in vitro translation of the mutant RNAs, identified a translation enhancing sequence (designated the translational enhancer domain or TED), comprising a conserved hairpin structure immediately downstream from the CP cistron (nucleotide 632 to nucleotide 749 for STNV-2) [Danthinne et al., *Mol. Cell. Biol.* 13: 3340–3349 (1993); Timmer et al., *J. Biol. Chem.* 13: 9504–9510 (1993)]. TED enhances in vitro translation when fused to a heterologous coding sequence (encoding beta-glucuronidase), but the level of enhancement depends on the nature of the 5' UTR and is larger in combination with the STNV 5' terminally located 173 nucleotides [Danthinne et al., supra (1993)]. It has been found that including an additional 11 bp of the STNV-2 sequence located immediately downstream of the conserved hairpin (nucleotide 632 to nucleotide 760 for STNV-2) into a second translation enhancing sequence enhances two-fold cap-independent translation in vitro of a heterologous coding sequence as compared to cap-independent translation conferred by a second translation enhancing sequence comprising the hairpin plus additional 4 nt of the STNV-2 sequence.

Preferred first translation enhancing sequences comprise the leader of STNV-2, especially preferred is a first translation enhancing sequence comprising the nucleotide sequence between nucleotide positions 1 and 32 of SEQ ID No.2, particularly preferred is a first translation enhancing sequence comprising the nucleotide sequence between nucleotide positions 1 and 38 of SEQ ID No.2 comprising an initiation codon and the second codon of the coat protein coding sequence.

Preferred second translation enhancing sequences comprise portions effective in enhancing translation of uncapped RNAs, derived from the trailer sequence of STNV-2, particularly the nucleotide sequence between nucleotide positions 632 and 753 of SEQ ID No.2, quite particularly the nucleotide sequence of SEQ ID No. 2 between nucleotide positions 632 and 760.

TNV is a small icosahedral plant virus, with a single genomic RNA of about 3.7 kb. The nucleotide sequence of different isolates has been published (except for some terminal nucleotides) [Meulewaeter et al. *Virology* 177:699–709 (1990); Coutts et al., *J. Gen. Virol.* 72: 1521–1529 (1991)]. Upon infection of plant cells, six TNV specific RNAs are produced: the genomic RNA, two subgenomic (sg) RNAs of 1.5 kb (sgRNA1; starts at nt 2184 of TNV-A) and 1.2 kb (sgRNA2; starts at nt 2461) which are 3' co-terminal, and the corresponding minus-strand RNAs. The RNA of TNV strain A (TNV-A) contains six major open reading frames (ORFs) and most likely serves as mRNA for the synthesis of a 23-kDa protein and a 82-kDa read-through protein, which are encoded by ORFs 1 and 2. In plants, the internal cistrons are most probably expressed from the two 3'-co-terminal subgenomic RNAs. The 5' ends of the largest and smallest subgenomic RNAs are located upstream of ORFs 3 and 5, respectively [Meulewaeter et al., *J. Virology* 66: 6419–6428 (1992)]. A very similar genome organization was proposed for TNV-D and for the carmovirus melon necrotic spot virus [Riviere and Rochon, *J. Gen. Virol.* 71: 1887–1896 (1990)]. The smallest subgenomic RNA probably directs the synthesis of the viral coat protein [Meulewaeter et al., *J. Virology* 66: 6419–6428 (1992)]. It comprises a 5' UTR of 152 nt, with a G content of only 11.8%, that precedes the start codon of the coat protein gene. The coat protein gene is followed by a trailer sequence of 241 nucleotides.

In the context of the invention, the inventors have identified translation enhancing sequences derived from the TNV-A virus. Preferred first translation enhancing sequences comprise portions derived from the 5' regions of TNV-A sgRNA2, such as the nucleotide sequence of SEQ ID No.1 between nucleotide positions 2461 and 2619, which still comprises 7 nucleotides of the coat protein coding sequence. Especially preferred is a first translation enhancing sequence comprising the nucleotide sequence between nucleotide positions 2461 and 2612 of SEQ ID No.1, particularly the nucleotide sequence between nucleotide positions 2461 and 2603 of SEQ ID No. 1, more particularly the nucleotide sequence between nucleotide positions 2461 and 2598 of SEQ ID No.1.

Preferred second translation enhancing sequences comprise portions effective in enhancing translation of uncapped RNAs, derived from the 3' region sequence of the TNV sgRNA2, particularly the nucleotide sequence between positions 3399 and 3684 of SEQ ID No.1, which still comprises 41 nucleotides upstream of the stop codon of the coat protein coding sequence, preferably the nucleotide sequence between nucleotide positions 3429 and 3611 of SEQ ID No.1, especially the nucleotide sequence between nucleotide positions 3472 and 3611 of SEQ ID No.1.

The translation enhancing sequences as derived from the 5' regions or 3' regions of an RNA plant virus can be modified by small insertions, deletions or substitutions, so that their capacity to enhance cap-independent translation or their synergistical interaction is not negatively affected. Such variants are referred to herein as "derivatives" and their use as enhancers for cap-independent translation form part of the invention. Generally, it is preferred that such a derivative has at least 90% sequence identity to the natural translation enhancing sequence.

For the purpose of this invention the % sequence identity of two related nucleotide or amino acid sequences refers to the number of positions in the two optimally aligned sequences which have identical residues (×100) divided by the number of positions compared. A gap, i.e., a position in an alignment where a residue is present in one sequence but not in the other is regarded as a position with non-identical residues.

It is however preferred, for optimal translation enhancing effect, that the nucleotide stretches which allow interactions between a pair of first and second translation enhancing sequences or between one or both of the translation enhancing sequences and the 3' end of the 18S rRNA, are left unchanged. For example, when using as first translation enhancing sequence the nucleotide sequence of SEQ ID No. 1 between nucleotide positions 2461 and 2619 and as second translation enhancing sequence the nucleotide sequence of SEQ ID No. 1 between nucleotide positions 3399 and 3684, the sequences of SEQ ID No. 1 between nucleotide positions 2464 and 2479, between nucleotide positions 2563 and 2567, between nucleotide positions 2571 and 2574, between nucleotide positions 2576 and 2586, between nucleotide positions 3449 and 3463, between nucleotide positions 3465 and 3472, and between nucleotide positions 3475 and 3482 are left unchanged.

For the same reason, when using as first translation enhancing sequence the nucleotide sequence of SEQ ID No. 2 between nucleotide positions 1 and 38, and as second translation enhancing sequence the nucleotide sequence of SEQ ID No. 2 between nucleotide positions 632 and 753, it is preferred that sequences of SEQ ID No. 2 between nucleotide positions 9 and 19, between nucleotide positions 24 and 30, between nucleotide positions 33 and 37, between nucleotide positions 636 and 640, between nucleotide positions 646 and 652, and between nucleotide positions 692 and 698 are left unchanged. Nevertheless, if one of these regions are changed, it is important to make the corresponding mutations in the appropriate complementary region.

To the extent that these sequences are included in the indicated alternative translation enhancing sequences, it is preferred that they are left unchanged to obtain optimal cap-independent translation with these sequences.

It is clear that first and second translation enhancing sequences may be derived from a different RNA virus, or from different genomic or subgenomic RNAs from the same virus. However, due to the fact that the first and second translation enhancing sequences often interact in enhancing cap-independent translation (e.g., when derived from STNV or TNV strains), it is preferred that first and second translation enhancing sequences are derived from the same genomic or subgenomic viral RNA.

Figure 2B:
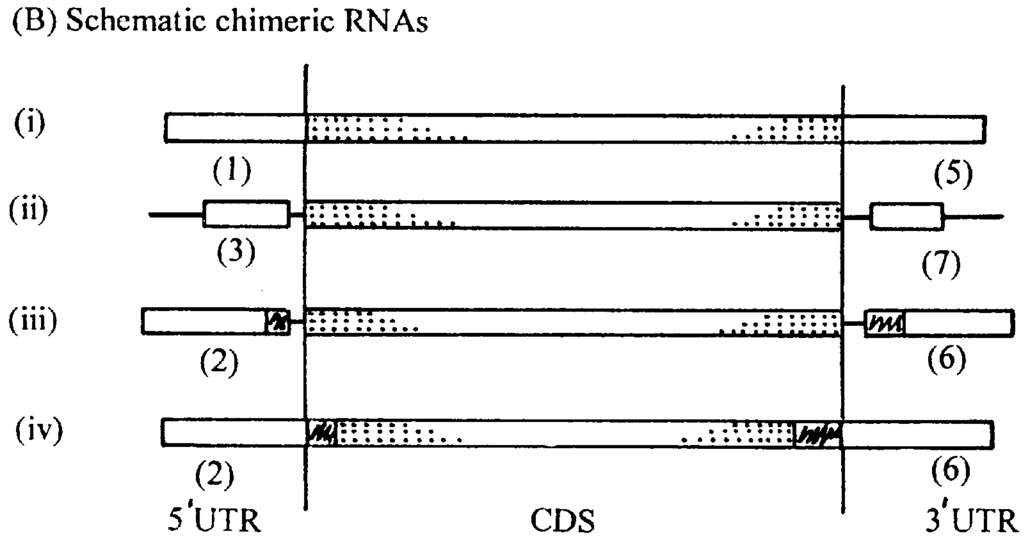
FIG. 2B is a schematic representation of different possible locations of first and second translation enhancing sequences with regard to the heterologous coding sequence and untranslated regions of the chimeric RNAs encoded by the cap-independently expressed chimearic genes of the invention.

Different possible positions of the first and second translation enhancing sequences in the chimeric RNAs encoded by the cap-independently expressed chimearic genes, with respect to the heterologous coding sequence and untranslated regions(indicated i to iv), are schematically represented in FIG. 2B. In this figure the heterologous coding sequence is indicated by a dotted bar. Translation enhancing sequences are indicated by the same bracketted arabic numbers as in FIG. 2A, and the portions of 5'UTR and 3' UTR and/or homologous coding sequence are indicated using the same color code as in FIG. 2B. Thick black lines refer to unrelated sequences, such as the intervening sequences between a first or a second translation enhancing sequence and the heterologous coding sequence.

It is preferred that a first translation enhancing sequence is located in the 5' region of the chimeric RNA transcribed from the CIG, particularly in the 5' UTR of the chimeric RNA(e.g., FIG. 2B i, ii and iii) or in a region surrounding the translation initiation codon of the heterologous sequence; in other words, the translation initiation codon may be comprised within the first translation enhancing sequence (e.g., FIG. 2B iv). Likewise it is preferred that a second translation enhancing sequence is located in the 3' region of the chimeric RNA transcribed from the CIG, particularly in the 3' UTR of the chimeric RNA(e.g., FIG. 2B i, ii and iii) or in a region surrounding the translation stop codon of the heterologous sequence; in other words the translation stop codon of the heterologous sequence may be comprised within the second translation enhancing sequence (e.g., FIG. 2B iv).

The first translation enhancing sequence may be located immediately upstream of the initiation codon of the coding sequence or it may be spaced therefrom by an intervening sequence of up to 100 nt, preferably up to 50 nt (see e.g., FIG. 2*b* ii and iii). Similarly the second translation enhancing sequence may be located immediately downstream of the stop codon of the coding sequence or it may be spaced therefrom by an intervening sequence of up to 100 nt, preferably up to 50 nt (see e.g., FIG. 2B ii and iii).

Moreover, for maximal translation enhancing effect, it may be necessary to make a translational fusion between a first translation enhancing sequence comprising nucleotide sequences extending immediately downstream of the initiation codon of the homologous coding sequences, and the coding sequence of interest (e.g., FIG. 2B iv). Likewise, it may be necessary to make a translational fusion between a second translation enhancing sequence, including nucleotide sequences extending immediately upstream of the initiation codon of the homologous coding sequences, and the coding sequence of interest (e.g., FIG. 2B iv).

For the purpose of the invention the term "translational enhancing sequence" refers to a part of an RNA molecule or RNA sequence, but may also be used to refer to a DNA molecule encoding such part.

The DNA regions encoding the translational enhancers used in this invention may be directly derived from a cDNA copy of the RNA from positive-stranded RNA viruses, but may also be partly or completely synthesized chemically.

It should be noted for unambiguousness that whenever a sequence is referred to as being the sequence between the nucleotide at position x and the nucleotide at position y, the resulting sequence includes both the nucleotide at position x and the nucleotide at position y. Moreover, as leaders and trailers evidently are parts of RNA molecules, while the sequences in the sequence listing refer to DNA molecules, it is clear that when it is stated in the description or the claims that a leader or trailer or translation enhancing sequence in an RNA comprises a nucleotide sequence as in the sequence listing, the nucleotide sequence referred to is actually the non-transcribed strand of the double-stranded DNA molecule presented in the sequence listing, which can be transcribed into the mentioned leader or trailer RNA. In other words, the actual base-sequence of the leader or trailer RNA molecule is identical to the base-sequence of the DNA molecule represented in the SEQ ID No referred to, except that thymine is replaced by uracil.

Further combinations of 5' regions and 3' regions derived from plant viruses, known in the art to stimulate translation of uncapped RNA in vitro include a leader and trailer from barley yellow dwarf virus serotype PAV [Wang and Miller *J. Biol. Chem.* 22: 13446–13452 (1995)]. Translation enhancing sequences derived from these 5' UTR and 3' UTR may also be used according to the invention.

The secondary structure prediction of the sequence of sgRNA2 from TNV-AC36 revealed that the conserved secondary structures between the trailer of TNV-A and TNV-AC36 correspond to the region comprising the second translation enhancing sequence of TNV-A. It is therefore expected that the 5' regions and 3' regions of the sgRNA2 from TNV-AC36 can be used according to the invention. Preferred first translation enhancing sequences of TNV-AC36 comprise the nucleotide sequence of SEQ ID No. 40, particularly the nucleotide sequence of SEQ ID N° 40 between nucleotide positions 1 and 90. Preferred second translation enhancing sequences comprise the nucleotide sequence of SEQ ID N° 41, particularly the nucleotide sequence of SEQ ID N° 41 between nucleotide positions 102 and 227.

CIGs of the invention encode an RNA comprising first and second translational enhancing sequences in their 5' and 3' regions, but these regions may include additional sequence elements. Whereas the presence of an intron in the 5'UTR, or a polyadenylation signal in the 3'UTR is less suitable for the present invention, the region surrounding the initiation codon of the CIG may be adapted to include e.g., plant translation initiation consensus sequences [Joshi, *Nucleic Acids Research* 15: 6643–6653 (1987)].

It is clear that the CIGs of the invention can further comprise one or more functional elements that can increase expression of the CIG, particularly increase the transcription of the CIG. Such functional elements include DNA sequences which enhance the accessibility of the promoter of the CIG for the cognate polymerase, such as DNA sequences influencing the local chromatin structure (scaffold attachment regions, matrix attachment regions as e.g., described by Breyne et al. [*The Plant Cell* 4: 463471 (1992)], Allen et al. [*The Plant Cell* 5: 603–613 (1993)] or in WO 94/07902).

The invention is especially useful for the efficient expression of AT-rich coding sequences, especially those encoding Bt ICPs, particularly native coding regions encoding Bt ICPs, integrated in the nuclear DNA of plants. Use of the methods and means of this invention, avoids many problems associated with the RNA polymerase II dependent expression of such genes. However, this invention can be used for the efficient expression of any gene. In this regard, the use of first and second translation enhancing sequences derived from TNV sgRNA2 to increase the production of heterologous gene products in plant cells, when combined with the efficient production of predominantly uncapped, non-polyadenylated transcripts by a bacteriophage single subunit RNA polymerase, such as T3 or T7 RNA polymerase, is particularly important. The present invention can therefore be used for the efficient production of any protein or polypeptide of interest by the use of a CIG comprising a suitable promoter such as T3 or T7 promoter, a DNA encoding a first translation enhancing sequence derived from STNV-2 or TNV sgRNA2, a DNA region encoding a heterologous protein or polypeptide of interest, a DNA encoding a second translation enhancing sequence derived from STNV-2 or TNV sgRNA2, and a terminator recognized by the used bacteriophage RNA polymerase. Transcription of the CIG by a single subunit RNA-polymerase such as T3 or T7 RNA polymerase, yields predominantly uncapped RNA without poly(A) tail that is efficiently translated due to the presence of the first and second translation enhancing sequences. Thus, a wide variety of peptides or proteins can be produced in plants using genes such as those coding for peptides or proteins with pharmaceutical interest, for seed proteins modified so as to enhance nutritional value or to include peptides of interest, for chaperoning, for bactericidal or bacteriostatic peptides. Also contemplated are genes which upon expression lead to plants having an increased resistance to herbicides (e.g., phosphinotricin, glyphosate, triazines), plants that can better withstand adverse environmental factors (e.g., high salt concentrations in the soil, extreme temperatures etc.), or plants that have enhanced phytopathogen resistance. The invention may also be used to express to a high level inhibitors to proteases, amylases or RNases (e.g., barnase-inhibiting barstar).

It goes without saying that to achieve the goal of this embodiment of the invention any viral single subunit polymerase and corresponding promoter can be used.

Preferably, the recombinant DNA comprising the CIGs also comprises a conventional chimeric marker gene. The chimeric marker gene can comprise a marker DNA that is under the control of, and operatively linked at its 5' end to, a promoter, preferably a constitutive plant-expressible promoter, such as a CaMV 35S promoter, or a light inducible promoter such as the promoter of the gene encoding the small subunit of Rubisco; and operatively linked at its 3' end to suitable plant transcription termination and polyadenylation signals. The marker DNA preferably encodes an RNA, protein or polypeptide which, when expressed in the cells of a plant, allows such cells to be readily separated from those cells in which the marker DNA is not expressed. The choice of the marker DNA is not critical, and any suitable marker DNA can be selected in a well known manner. For example, a marker DNA can encode a protein that provides a distinguishable color to the transformed plant cell, such as the Al gene (Meyer et al. (1987), *Nature* 330: 677), can encode a fluorescent protein [Chalfie et al, *Science* 263: 802–805 (1994); Crameri et al, *Nature Biotechnology* 14: 315–319 (1996)], can encode a protein that provides herbicide resistance to the transformed plant cell, such as the bar gene, encoding PAT which provides resistance to phosphinothricin (EP 0242246), or can encode a protein that provides antibiotic resistance to the transformed cells, such as the aac(6') gene, encoding GAT which provides resistance to gentamycin (WO 94/01560).

In an alternative embodiment, the marker gene could be operably linked to similar expression controls, i.e., promoter, first and second translation enhancing sequences and terminator as used for the CIG, thereby allowing direct selection for transgenic cell lines wherein cap-independent translation occurs very efficiently.

In transgenic plants the chimeric polymerase gene is preferably in the same genetic locus as the CIG so as to ensure their joint segregation. This can be obtained by combining both chimeric genes on a single transforming DNA, such as a vector or as part of the same T-DNA. However, a joint segregation is not always desirable. Therefore both constructs can be present on separate transforming DNAs, so that transformation might result in the integration of the two constructs at different locations in the plant genome, or even in seperate lines, which subsequently have to be crossed to yield a hybrid plant whereby the CIG and chimeric polymerase are joined in a single cell.

In accordance with the present invention, a plant expressing a chimeric gene in a cap-independent manner, can be obtained from a single plant cell by transforming the cell in a known manner, resulting in the stable incorporation of a cap-independently expressed chimeric gene of the invention into the nuclear genome.

A recombinant DNA of the invention, i.e., a recombinant DNA comprising a CIG, a chimeric polymerase gene and/or a chimeric marker gene can be incorporated in the nuclear DNA of a cell of a plant, particularly a plant that is susceptible to Agrobacterium-mediated transformation.

Gene transfer can be carried out with a vector that is a disarmed Ti-plasmid, comprising the recombinant DNA of the invention, and carried by Agrobacterium. This transformation can be carried out using the procedures described, for example, in EP 0116718. Ti-plasmid vector systems comprise the recombinant DNA of the invention between the T-DNA border sequences, or at least to the left of the right T-DNA border. Alternatively, any other type of vector can be used to transform the plant cell, applying methods such as direct gene transfer (as described, for example, in EP 0233247), pollen-mediated transformation (as described, for example, in EP 0270356, W085/01856 and U.S. Pat. No. 4,684,611), plant RNA virus-mediated transformation (as described, for example, in EP 0067553 and U.S. Pat. No. 4,407,956), liposome-mediated transformation (as described, for example, in U.S. Pat. No. 4,536,475), and the like.

Other methods, such as microprojectile bombardment as described, for example, by Fromm et al. [(1990), *Bio/Technology* 8: 833] and Gordon-Kamm et al. [(1990), *The Plant Cell* 2: 603], are suitable as well. Cells of monocotyledonous plants, such as the major cereals, can also be transformed using wounded or enzyme-degraded intact tissue (such as immature seedlings in corn) or the embryogenic callus obtained therefrom (such as type I callus of corn), as described in WO 92/09696. Corn protoplasts can be transformed using the methods of EP 0469273. The resulting transformed plant cell can then be used to regenerate a transformed plant in a conventional manner.

The obtained transformed plant can be used in a conventional breeding scheme to produce more transformed plants with the same characteristics or to introduce the cap-independently expressed chimeric gene or the chimeric polymerase gene of the invention, or both in other varieties of the same or related plant species. Seeds obtained from the transformed plants contain the CIG of the invention as a stable genomic insert.

The transgenic plant according to the invention may be a dicotyledonous or a monocotyledonous plant. Preferred dicotyledonous plants are potato, tomato, cotton, selected Brassica species such as oilseed rape, tobacco, soybean. Preferred monocotyledonous plants are corn, wheat, rice and barley.

The following examples provide additional description of the identification of translation enhancing sequences derived from TNV sgRNA2, the use of such translation enhancing sequences derived from necroviruses to stimulate expression in vitro and in vivo of heterologous genes (comprising genes with native coding sequences coding for Bt ICPs), construction of plant transformation vectors comprising CIGs including DNA copies of said translation enhancing elements of necroviruses, further operably linked to a promoter region recognized by a RNA polymerase capable of producing predominantly uncapped, non-polyadenylated RNA, and the use of such vectors to obtain plant cells and plants comprising CIGs, further comprising an RNA polymerase capable of producing uncapped, non-polyadenylated RNA. These examples are not intended to unduly restrict the invention to the uses described therein. Throughout these examples the following materials and methods were employed, unless stated otherwise:

In vitro transcription of uncapped and capped RNAs. Uncapped RNAs were produced by in vitro transcription of linear DNA templates (either plasmids treated with restriction enzymes, or polymerase chain reaction (PCR) fragments) containing the appropriate promoter region, using T7 RNA polymerase (Pharmacia, Upsala Sweden) or T3 RNA polymerase (Pharmacia), essentially as described by Krieg and Melton, *Nucl. Acid Res* 12:7057–7070 (1984), modified in that after 90 min of incubation at 37° C., extra NTPs (0.5 mM) and RNA polymerase (0.3 U/$\mu$l) were added, and the reaction was further incubated for 60 min at 37° C. After reaction the DNA template was removed by adding 1.5 U/$\mu$l DNaseI (Pharmacia, Upsalla, Sweden) and incubating further for 10 min at 37° C.

Subsequently, the mixture was purified by phenol extraction, and passed through a Sephadex G-50 column (Pharmacia, Upsalla, Sweden). RNA was precipitated in 0.09 M K-acetate and 66% ethanol, and resuspended in RNase-free $H_2O$. RNA concentration was determined by measuring $OD_{260}$. The integrity of the transcripts was verified by formaldehyde-agarose gel-electrophoresis. Capped RNAs were obtained by modifying the reaction conditions to include 0.5 mM $^{m7}$GpppG and 0.05 mM GTP, during the first 30 minutes of incubation.

In vitro translation of RNAs and computer aided data analysis.

Cell-free translation of in vitro synthesized RNA transcripts was performed in a wheat germ extract prepared according to Morch et al., Methods. *Enzymol* 118:154–164 (1986), using final concentrations of 1 mM $Mg^{2+}$, and 110 mM $K^+$. Reactions were performed with 3 pmol of transcript, in a total volume of 75 $\mu$l in the presence of [$^{35}$S] methionine. To determine protein accumulation profiles, aliquots were taken at 6 to 8 different time points, and reaction products were separated on 0.1%SDS-12.5% polyacrylamide gels as described by Laemmli, *Nature* 227: 680–685, (1970). After electrophoresis, gels were fixed overnight at 4° C. in a 30% methanol-7% acetic acid mixture, dried and autoradiographed. Quantification of in vitro synthesized proteins was performed by slicing the appropriate band from the gel, and measuring the incorporated radioactivity by liquid scintillation counting. The obtained values were normalized to the number of methionine residues present in the synthesized protein, excluding the initiatior methionine. RNA degradation (chemical half-life of RNA) was analyzed and quantified as described by Danthinne et al., *Mol. Cell. Biol.* 13: 3340–3349 (1993).

Protein accumulation (P) in function of time (t) was analyzed using the mathematical description P(t)=A. t½/In2 (1−e$^{-In}$2(t−7)/t½) described by Danthinne et al (1993; supra) in which T corresponds to the time point at which the first translation product is completed, A is the translation efficiency of the mRNA and t½ is the functional half-life of the mRNA. From this formula, it can be deduced that P(∞)=A. t½/In2, showing that the protein peak level is proportional to both the translation efficiency and the functional half-life of the mRNA. The parameters A, t½, and T were estimated by nonlinear regression using the GraphPad Prism software® version 1.02.

Introduction of RNA in tobacco protoplasts by electroporation.

Isolation of mesophyll protoplasts from leaves of Nicotiana tabacum cv Petit Havanna SRI was carried out as described by Denecke et al., *Methods Mol. Cell. Biol.* 1:19–27 (1989) except that before electroporation, the protoplasts were washed once with TEX-buffer and three times with electroporation buffer. Introduction of RNA into the protoplasts was carried out by electroporation in the presence of 10–15 pmol of RNA per $10^6$ protoplasts in 300 $\mu$l. Electroporation was performed immediately after the addition of the protoplasts to the RNA. For RNAs including STNV translation enhancing sequences and replication sequences 1 pmol of RNA was used and 0.2 pmol of TNV RNA was added. Electroporation was done, using the following electrical parameters: Capacitance (C)=200 μF, initial field strength ($E_0$)=630 V/cm. After electroporation, protoplasts were diluted 10-fold in TEX-buffer, floated by centrifugation, isolated and diluted with TEX-medium until a concentration of $0.5 \times 10^6$ protoplasts per ml was reached. Aliquots of an appropriate amount of protoplasts (e.g. $5 \times 10^6$) were incubated at 25° C. in the dark for different times before processing.

Analysis of the fate of the RNA after Introduction in tobacco protoplasts, detection of the different In vivo translation products and computer-aided data analysis of the accumulation profiles.

RNA from protoplasts was prepared as described by Denecke et al (1993) supra. Quantitative Northern analysis was performed as described by Meulewaeter et al., supra (1992). Alternatively, RNA quantification was performed by densitometric scanning of the autoradiograph resulting from the Northern hybridization using a DT120 laser scanner and analysing the data with the Molecular Dynamics ImageQuant version 4.2 software.

Proteins were isolated from tobacco protoplasts by 10 seconds sonication (using a Soniprep 150, MSE Scientific Instruments, Crawley, England) in an extraction buffer consisting either of 50 mM Tris/HCl, 2 mM EDTA, 0.15 μg/μl DTT, 0.15 μg/μl BSA and 30 μg/μl PMSF (for protoplasts wherein PAT and chloramphenicol acetyltransferase (CAT) encoding transcripts were introduced) or of 50 mM Tris/HCl, 5% glycerol, 100 mM KCl, 1 mM benzamidine HCl, mM ε-amino-n-caproic acid, 10 mM EDTA, 10 mM EGTA, 1 μg/ml antipain, 1 μg/ml leupeptin, 14 mM β-mercaptoethanol and 1 mM PMSF (for protoplasts wherein Bt ICP encoding transcripts were introduced). The lysate was centrifuged 5 min at 10000 g and the supernatants were recovered. Protein concentrations were determined according to Bradford (1976). PAT activities were determined with 10 μg of soluble protein, using the chromatography method of De Block et al., *EMBO J.* 6:2513–2518 (1987).

Quantification was performed by densitometric scanning of the autoradiograph using a DT120 laser scanner and analysing the data with the Molecular Dynamics ImageQuant version 4.2 software.

CAT activity was determined by thin-layer chromatography CAT assays as described by Gorman et al., *Mol. Cell. Biol.* 2:1044–1051 (1982) and quantified either by liquid-scintillation counting of excised spots or by densitometric scanning of the autoradiograph using a DT120 laser scanner and analysing the data with the Molecular Dynamics ImageQuant version 4.2 software. Absolute levels of CAT protein were calculated using a standard curve of purified CAT protein. Bt ICPs were detected by ELISA, as described by Clark et al., *Meth Enzymol.* 118: 742–766 (1986).

The translational efficiency (z) of a replicating RNA can be described by the mathematical function:

$z=(dP/dt)(In2/t_{1/2})/(dR/dt)$ in which R represents total RNA pool, P corresponds to protein concentration and $t_{1/2}$ is the functional half-life of the RNA. (dP/dt)/(dR/dt) can be estimated by non-linear regression using GraphPad Prism™ software version 1.02.

Unless stated otherwise in the Examples, all recombinant DNA techniques are carried out according to standard protocols as described in Sambrook et al. (1989) *Molecular Cloning: A Laboratory Manual*, Second Edition, Cold Spring Harbor Laboratory Press, NY and in Volumes 1 and 2 of Ausubel et al. (1994) *Current Protocols in Molecular Biology, Current Protocols*, USA. Standard materials and methods for plant molecular work are described in *Plant Molecular Biology Labfax* (1993) by R. D. D. Croy, jointly published by BIOS Scientific Publications Ltd (UK) and Blackwell Scientific Publications, UK. These publications also include lists explaining the current abbreviations.

In the examples and in the description of the invention, reference is made to the following sequences of the Sequence Listing:

SEQ ID No.1: cDNA of TNV-A
SEQ ID No.2: cDNA of STNV-2
SEQ ID No.3: cat-gene
SEQ ID No.4: inserted DNA fragment in pXD324
SEQ ID No.5: native coding sequence of cry9C (truncated)
SEQ ID No.6: native coding sequence of cry1A(b) (truncated)
SEQ ID No.7: oligonucleotide FM10
SEQ ID No.8: oligonucleotide FM11
SEQ ID No.9: oligonucleotide FM8
SEQ ID No.10: oligonucleotide FM9
SEQ ID No.11: oligonucleotide FM12
SEQ ID No.12: oligonucleotide FM16
SEQ ID No.13: oligonucleotide FM17
SEQ ID No.14: oligonucleotide FM18
SEQ ID No.15: oligonucleotide FM19
SEQ ID No.16: oligonucleotide FM20
SEQ ID No.17: oligonucleotide FM21
SEQ ID No.18: oligonucleotide FM23
SEQ ID No.19: oligonucleotide FM24
SEQ ID No.20: oligonucleotide FM1
SEQ ID No.21: oligonucleotide FM13
SEQ ID No.22: oligonucleotide FM14
SEQ ID No.23: oligonucleotide FM15
SEQ ID No.24: T3 RNA polymerase terminator
SEQ ID No.25: oligonucleotide FM3
SEQ ID No.26: oligonucleotide FM4
SEQ ID No.27: oligonucleotide FM5
SEQ ID No.28: oligonucleotide FM7
SEQ ID No.29: oligonucleotide FM6
SEQ ID No.30: oligonucleotide FM22
SEQ ID No.31: oligonucleotide FM25
SEQ ID No.32: oligonucleotide FM26
SEQ ID No.33: oligonucleotide FM2
SEQ ID No.34: synthetic DNA fragment encoding cry9C (truncated)
SEQ ID No.35: inserted DNA fragment of pFM409
SEQ ID No.36: nucleotide sequence preceding the T7 RNA polymerase in pFM410
SEQ ID No.37: nucleotide sequence of pTFM600 T-DNA
SEQ ID No.38: nptII coding region translationally fused to coat protein coding sequence and preceded by STNV-2 leader
SEQ ID No.39: nptII coding region flanked by suitable restriction sites
SEQ ID No.40: 5' UTR of TNV-AC36
SEQ ID No.41: 3' UTR of TNV-AC36

EXAMPLE 1

Plasmid Constructions Used For in Vitro Transciption to Generate the Test RNAs Used For the in Vitro and in Vivo Translation Experiments pFM20, pFM21, pFM23 and pFM24 are in vitro transcription plasmids containing original TNV-A cDNA fragments cloned in the SmaI site of pGEM®-3Z (Promega Biotec., Madison, Wis.) as described by Meulewaeter et al., supra (1990). pFM20 contains the nucleotide sequence between nucleotide 1763 and 3660 of SEQ ID No.1; pFM21 contains a cDNA corresponding to the nucleotide sequence between nucleotide 20 and 2619 of SEQ ID No.1; pFM23 contains a cDNA corresponding to the nucleotide sequence between nucleotide 2593 and 3510 of SEQ ID No.1; and pFM24 contains a cDNA corresponding to the nucleotide sequence between nucleotide 19 and 1632 of SEQ ID No.1.

pFM33 is a 3'-terminal TNV-A cDNA clone in the ScaI site of pAT153. The cDNA was synthesized on TNV dsRNA as described by Danthinne et al., supra (1991). The cDNA clone contains the nucleotide sequence between 3334 and 3684 of SEQ ID No.1, followed by three A-residues. pAT153 is a derivative of pBR322 lacking the 0.62 kb HaeII B-fragment [Twiggs and Sherait, *Nature* 283:216–218, (1980)].

pFM136 [(Meulewaeter et al., supra (1992)] contains the cat coding sequence of Tn9, flanked by additional nucleotides on a fragment having the sequence of SEQ ID No.3, cloned as an XbaI, filled-in ClaI fragment between the XbaI and trimmed KpnI sites of pGEM®-3Z.

pFM133 and pFM134 were made by insertion of the bar coding region as a filled-in BamHI fragment from pGEMBAR into the trimmed SacI site of pFM23 and pFM20, respectively, in such a way that upon transcription with T7 RNA polymerase an RNA encoding PAT is produced. pGEMBAR is a clone of a modified BamHI fragment of pGSR1 (EP 242236), comprising the coding sequence of the bar gene, wherein the sequence around the initiation codon (CCAIQA) has been changed into a NcoI restriction recognition sequence (CCAMIG). This BamHI fragment has been cloned into the BamHI site of pGEM®-1.

Insertion of the 1426-bp blunt-ended EcoRI-PvuI fragment of pFM134 into the blunt-ended SacI fragment of pFM136 resulted in plasmid pFM140.

pFM139 was obtained by the insertion of the cat gene, as a PstI, blunt-ended SacI fragment from pFM136, between the PstI and blunt-ended MluI sites of pFM134.

A translational fusion between the TNV coat protein and the cat open reading frames was made by transfer of the 830-bp filled-in BamHI fragment from pFM2.1 into the trimmed SacI site of pFM136. A 1371 bp PstI-NsiI fragment from the resulting plasmid was inserted between the PstI and NsiI sites of pFM134 in such a way that both sites are restored, resulting in plasmid pFM138.

pXD324 contains downstream of the T7 promoter: the -fragment of tobacco mosaic virus, the bar coding region, a poly(dA/dT) track of about 100 residues, and the SP6 promoter. This plasmid is composed of the following nucleotide sequence: from nucleotide 1 to 790 it contains the nucleotide sequence of SEQ ID No.4; from nucleotide 791 to 1221 it contains the sequence complementary to the sequence between nucleotides 2865 and 2435 of pGEM®-1 (Promega Biotec., Madison, Wis.); from nucleotide 1222 to 3696 it contains the nucleotide sequence between the nucleotide at position 269 and the nucleotide at position 2743 of pGEM®-3Z.

pFM108 is pGEM®-3Z derivative that, by deletion of the sequence between the nucleotide at position 2 and the nucleotide at position 17, contains a KpnI site at the start of transcription of the T7 promoter [Danthinne et al.,supra (1993)].

pXD535 is an in vitro transcription plasmid that contains a full-length STNV-2 cDNA clone except for the first nucleotide (sequence as in SEQ ID No.2 between the nucleotide at position 2 and the nucleotide at position 1245, downstream of the T7 promoter [Danthinne et al., supra (1993)]. The STNV-2 cDNA was cloned between the SmaI and trimmed KpnI sites of a plasmid obtained by cloning of the 515-bp long AatII-PstI fragment of pFM108 between the AatII and PstI sites of pAT153.

pGEM4N is a derivative of pGEM®-4 (Promega Biotec., Madison, Wis.) obtained by digestion with HindIII, filling-in, and religating. In this way, an NheI site is created.

A KpnI-NheI fragment containing codons 44 to 666 of the cry9C coding region flanked by translation initiation and termination sites (nucleotide sequence between nucleotide 6 and 1892 of SEQ ID No.5), was cloned between the KpnI and NheI sites of pGEM4N, resulting in plasmid pGEM9C1.

pGEM9C2 is a similar plasmid containing a synthetic coding region for the codons 44 to 666 of cry9C flanked by translation initiation and termination sites. The cry9C encoding NcoI-NheI fragment of pGEM9C1 has been exchanged for the NcoI-NheI fragment comprising the synthetic coding region, which has the nucleotide sequence between nucleotide 8 and 1888 of SEQ ID No. 34).

A NcoI-NheI fragment containing codons 29 to 616 of the cry1Ab5 coding region flanked by transation initiation and termination sites (nucleotide sequence between nucleotide 8 and 1783 of SEQ ID No.6), was cloned between the NcoI and NheI sites of pGEM9C1, resulting in plasmid pGEM1Ab1.

Plasmid pAB02 was constructed as follows: a PCR fragment, obtained with primers FM10 and FM11 having the nucleotide sequences of SEQ ID No.7 and SEQ ID No.8, using plasmid pFM20 as template, was digested with BamHI (in first primer) and BsmI and cloned between the BsmI and BamHI sites of pFM20, resulting in plasmid pFM187. This plasmid now contains a BsaI site at the 5' end of the TNV sgRNA2 sequence. The 5' end of the subgenomic RNA2 was fused to the T7 promoter by cloning the 1224-bp BsaI(filled-in)-PstI fragment of pFM187 between the KpnI (blunted) and PstI site of pFM108, resulting in plasmid pFM187B. The 3' end of TNV sgRNA2 was reconstructed by PCR using primers FM8 and FM9 having the nucleotide sequences of SEQ ID No.9 and SEQ ID No.10 with pFM33 as template. The amplified fragment was digested with PstI and Bsu36I and cloned between the PstI and Bsu36I sites of pFM20 and pFM187B, resulting in plasmids pFM20C and pAB02, respectively.

pRD01 was created by restricting pAB02 with EcoRI, followed by filling-in the protruding termini with Klenow polymerase and religation. This creates a new stop codon at nucleotide 735 of the TNV-A CP mRNA (nucleotide 3195 of SEQ ID No. 1). The RNA specified by this plasmid encodes a C-terminally truncated CP protein of 21-kDa.

Plasmids pRD02, pRD06, pRD03, pRD04, and pRD05 were created as follows. pRD01 contains a unique BstBI site immediately downstream of the newly introduced stop codon. pRD01 was restricted by BstBI and respectively one of the following enzymes: Asp718, NheI, BsaAI, Bsu36I, and BamHI. The linearized DNA fragments were treated with Klenow polymerase and religated.

Plasmid pAB01 was constructed by cloning the 592-bp NdeI-BsmI fragment of pFM23 between the NdeI and BsmI sites of pAB02.

Plasmid pMA300 [Andriessen et al., *Virology* 212: 22–224 (1995)] was constructed in two steps starting with plasmid pFM24. The intact 5'end of the TNV-A sequence was reconstructed using complementary oligomers encoding the first 35 nucleotides of TNV-A (nucleotide sequence between nucleotide 1 and 35 of SEQ ID No.1) to create plasmid pFM39. A fragment from plasmid pFM21 containing TNV-A residues 311 to 2619 (nucleotide sequence of SEQ ID No.1 between the nucleotides at position 311 and 2619) was inserted in pFM39.

pTNV was constructed as follows: the 1636-bp NsiI-HindIII fragment of pFM20C was cloned between the NsiI and HindIII sites of pMA300, resulting in plasmid pTNV. pTNV contains the full-length TNV-A sequence under control of a T7 promoter. Upon digestion with BsaI, T7 RNA polymerase directs the synthesis of a transcript that differs from the natural RNA only by the addition at the 5'-end of an extra G residue.

Plasmids to obtain chimeric TNV-cat RNAs were constructed as follows. A PCR fragment obtained with primers FM10 and FM12 having the nucleotide sequences of SEQ ID No.7 and SEQ ID No.11, using plasmid pFM140 as template, was digested with BamHI (present in the first primer) and BspEI (present in the cat gene) and cloned between the BspEI and BamHI sites of pFM140, resulting in plasmid pFM188. This plasmid contains a BsaI site at the 5' end of the TNVsgRNA2 leader sequence.

The 5'end of the TNVsgRNA2 was fused to the T7 promoter by cloning the 929-bp BsaI(filled-in)-PstI fragment of pFM188 between the KpnI (blunted) and PstI site of pFM108. This resulted in plasmid pFM188B.

The 1006-bp NarI-NlaIV fragment of pFM188B was cloned between the BsaAI and NarI site of pAB02, resulting in plasmid pFM188C.

The 1335-bp NsiI-XbaI fragment of pFM138 was ligated to the 5097-bp NsiI-NheI fragment of pTNV, resulting in plasmid pFM216.

The 1155-bp PvuI-PstI fragment of pFM216 was ligated to the 2830-bp PvuI (partially digested)-PstI fragment of pAB02, resulting in plasmid pFM188G.

The 891-bp NcoI-NdeI fragment of pFM188B was ligated to the 3072-bp NcoI-NdeI fragment of pFM216, resulting in plasmid pFM188H.

Similarly, the 768-bp NcoI-NdeI fragment of pFM136 was ligated to the 3072-bp NcoI-NdeI fragment of pFM216, resulting in plasmid pFM1881.

A PCR fragment was obtained with primers FM23 and FM24 having the nucleotide sequences of SEQ ID No.18 and SEQ ID No.19, using plasmid pFM188C as a template, digested with EcoRI and NdeI and cloned between the EcoRI and NdeI sites of pFM188C, resulting in plasmid pVE190. In this way the T7 promoter of pFM188C was exchanged for a T3 promoter.

Using pFM188C as template, DNA fragments were PCR-amplified with primers FM16 and FM17 having the nucleotide sequences of SEQ ID No.12 and SEQ ID No.13, and with primers FM18 and FM19 having the nucleotide sequences of SEQ ID No.14 and SEQ ID No.15. Both fragments were then used in an overlap extension PCR with primers FM16 and FM19, having the nucleotide sequences of SEQ ID No.12 and SEQ ID No.15 to amplify a DNA fragment containing an NheI site just downstream of the cat stop codon. The amplified fragment was digested with NcoI and BamHI and cloned between the NcoI and BamHI site of pFM188C, resulting in plasmid pVE192.

Using pFM188C as template, DNA fragments were amplified with primers FM16 and FM21, having the nucleotide sequences of SEQ ID No.12 and of SEQ ID No.17, and with primers FM20 and FM19, having the nucleotide sequences of SEQ ID No.16 and SEQ ID No.15. Both fragments were then used in an overlap extension PCR with primers FM16 and FM19, having the nucleotide sequences of SEQ ID No.12 and SEQ ID No.15 to amplify a DNA fragment containing an NheI site at nucleotide963–968 of TNV sgRNA2 (nucleotides 3423–3428 of SEQ ID No.1). The amplified fragment was digested with NcoI and BamHI and cloned between the NcoI and BamHI sites of pFM188C, resulting in plasmid pVE193.

The 1037-bp NdeI-NheI fragment of pVE192 was cloned between the NdeI and NheI sites of pVE193, resulting in plasmid pVE195. pVE192 was digested with NheI and Bsu36I, blunted, and religated, resulting in plasmid pVE196.

Plasmids to obtain chimeric STNV-cat RNAs were constructed in the following way. pFM175, which contains the first 889 nucleotides of the STNV-2 cDNA downstream of the T7 promoter, was made by insertion of the 1123-bp NdeI-NsiI fragment of pXD535 between the PstI and NdeI sites of a pGEM®-3Z derivative that lacks the sequence between the nucleotide at position 62 and the nucleotide at position 91, including the SP6 promoter.

A mutant STNV leader (designated STNV*) was cloned downstream of the T7 promoter by insertion of the annealed oligodeoxyribonucleotides FM14 and FM15, having the nucleotide sequences of SEQ ID No.22 and SEQ ID No.23 between the SmaI and trimmed KpnI sites of pFM108, resulting in plasmid pFM184A. The STNV* leader was subsequently fused to the cat coding region by insertion of the 520-bp NcoI(filled-in)NdeI fragment of pFM184A between the NdeI and blunted BssHII sites of pFM139, resulting in plasmid pFM189.

In pFM191, the cat coding region was placed upstream of the TED of STNV-2 ($TED_2$) by insertion of the 900-bp NarI-NlaIV fragment of pFM189 between the NarI and blunted NcoI sites of pFM175.

pFM169 was made by inserting the cat coding region, as a PstI-NruI fragment of pFM136 between the PstI and filled-in XbaI sites of pXD324. Insertion of the 430-nt-long NcoI-SphI fragment of pFM191 between the NcoI and SphI sites of pFM169 yielded plasmid pFM191A. A derivative of pXD324, named pFM179, was made by religating blunt-ended HindIII-digested plasmid. Upon linearization of the resulting plasmid with NheI, RNA is synthesized which has GCUAG downstream of the poly(A) tail. The poly(dA:dT)-track of pFM179 was placed downstream of TED by inserting the 1100-nt-long SpeI-NdeI fragment of pFM191A between the XbaI and NdeI sites of pFM179. The resulting plasmid was named pFM209. The length of the poly(dA:dT) track of pFM191A and pFM209 was estimated by polyacrylamide gel electrophoresis to be about 100 bp.

pFM191B was made by inserting the 430-nt long NcoI-SphI fragment of pFM191 between the NcoI and SphI sites of pFM136.

To fuse the STNV-2 leader to the cat coding region, a fragment containing the T7 promoter fused to the first 38 nucleotides of the STNV-2 cDNA was amplified by PCR on pFM175 using primers FM1 and FM13, having the nucleotide sequences of SEQ ID No.20 and SEQ ID No.21. After digestion with MluI and NdeI, this fragment was cloned between the BssHII and NdeI sites of pFM189 and pFM191, resulting in plasmids pFM189A and pFM191E, respectively.

Plasmid pFM207E was constructed by ligating the 726 bp PvuII-AflIII fragment from pFM191E and the 615 bp long PvuII-EcoRI fragment of pFM191 in the 2556 bp EcoRI-AflIII vector fragment from pFM191E.

Plasmids to obtain chimeric STNV-cry RNAs, were obtained in several steps as outlined. The 1496-bp long NdeI-HindII fragment of pXD535 was cloned between the NdeI and Eco47III sites of pXD324, resulting in plasmid pFM214. A PCR fragment obtained with primers FM1 and FM3 having the nucleotide sequences of SEQ ID No.20 and SEQ ID No.25, using plasmid pFM175 as a template, was digested with NcoI and NdeI and the resulting fragment was cloned between the NcoI and NdeI sites of pFM214, yielding plasmid pFM214C. A synthetic DNA fragment, consisting of the annealed oligodeoxyribonucleotides FM4 and FM5, having the nucleotide sequences of SEQ ID No.26 and SEQ ID No.27, was cloned between the BsaAI and NcoI sites of pFM214C, resulting in plasmid pFM214A. pFM214A was used as template in a PCR reaction with the primers FM1 and FM7, having the nucleotide sequence of SEQ ID No.20 and SEQ ID No.28 and the resulting fragment was digested with NdeI and NcoI. This fragment was cloned, together with the 1880-bp NcoI-NheI fragment of pGEM9C1, between the NheI and NdeI sites of pFM214A. The resulting plasmid was designated as pRVL11. pRVL12 was obtained by the same strategy except that the NcoI-NheI fragment of pGEM9C2, comprising a synthetic coding region of cry9C was used.

EXAMPLE 2

STNV-2 5'UTR and $TED_2$ Cooperate in Stimulating Cap-Independent Translation of Heterologous mRNAs in Vivo The first set of experiments demonstrate that 5' information affecting translation is contained within the 5'-terminal 38 nt of STNV-2, comprising the full sequence complementarity with $TED_2$. Translation of an RNA which has the STNV-2 leader plus the first two codons of the CP coding region (further named STNV-2 leader) translationally fused to the cat coding region was compared to that of an analogous RNA with a mutated leader (STNV* leader) which has a reduced complementarity with $TED_2$. Translation of the RNA with the STNV-2 leader was not affected by the presence of a cap structure, whereas the RNA with the STNV* leader required the cap to maintain its functional stability (Table 1). These data show that the functional stability of the STNV-2 RNA in vitro depends on the combined presence of the 5'-terminal 38 nucleotides (nt) and $TED_2$. Furthermore, it establishes that the complementarity between leader and TED is important for the functional stability of the mRNA.

TABLE 1

The 5'-terminal 38 nt of STNV-2 cooperate with TED to maintain the functional stability of the mRNA in vitro.

| Template DNA | Leader | cap | T.E. (cpm/met.min) | $t_{1/2}$ (min) | Peak Level (cpm/met) |
|---|---|---|---|---|---|
| pFM191 (SpeI) | STNV* | − | 48.2 ± 3.8 | 17.4 ± 1.9 | 1210 |
| pFM191 (SpeI) | STNV* | + | 59.6 ± 1.1 | 31.7 ± 1.1 | 2726 |
| pFM191E (SpeI) | STNV-2 | − | 46.2 ± 6.4 | 55.1 ± 21.2 | 3673 |
| pFM191E (SpeI) | STNV-2 | + | 46.7 ± 6.7 | 47.7 ± 18.9 | 3214 |

It was demonstrated that inclusion of a second translation enhancing sequence comprising $TED_2$ followed by the sequence between nt 753 and 760 of the STNV-2 trailer in the RNA further increased translation of uncapped RNAs in vitro. Template DNAs for in vitro transcription by T7 RNA polymerase were made by PCR using appropriate primers with plasmid pFM191B as template. The resulting RNAs contain a 19 nt leader derived from a polylinker sequence, the cat coding region, and varying parts of the STNV-2 trailer (see Table 1b). The RNAs were translated in a wheat germ extract. CAT protein accumulation was quantified after 18, 25, 32, 40, 50, 65, 80, and 100 min of incubation. Estimation of the translation efficiency and functional half-life of the mRNAs from these data (see Table 1bis) showed that translation of the RNA which has 7 additional STNV-2 nucleotides downstream of $TED_2$ was about two-fold higher than translation of an RNA which has only $TED_2$ as trailer.

TABLE 1bis

STNV-2 sequences downstream of TED increase cap-independent translation of cat RNAs in vitro.

| RNA | Relevant features: 5'UTR | Relevant features: 3'UTR | T.E. (k.mol/min) | $t_{1/2}$(min) | Peak level (k.mol) |
|---|---|---|---|---|---|
| 1 | 19 nt | nt 632–753 of STNV-2 (=$TED_2$) | 90.1 ± 8.1 | 42.5 ± 8.1 | 5524 |
| 2 | 19 nt | nt 632–760 of STNV-2 | 166.1 ± 18.1 | 37.8 ± 8.1 | 9058 |

The effect of $TED_2$ (second translation enhancing sequence from STNV-2), as defined in vitro, on translation of a series of chimeric cat RNAs was determined in tobacco protoplasts.

In vitro transcription by T7 RNA polymerase on the different templates (summarized in Table 2) was used to generate the RNAs introduced in tobacco protoplasts (45 pmol cat-comprising RNA per $3\times10^6$ tobacco protoplasts). The levels of generated CAT protein were determined 5.5 hrs after RNA introduction. They are summarized in Table 2.

TABLE 2

$TED_2$ stimulation of uncapped and capped heterologous mRNAs in tobacco protoplasts

| Template DNA | Relevant features: 5'UTR | Relevant features: 3'UTR | CAT level (pg/100 μg total protein): uncapped | CAT level (pg/100 μg total protein): capped | Normalized translation stimulation by $TED_2$: uncapped | Normalized translation stimulation by $TED_2$: capped |
|---|---|---|---|---|---|---|
| $pFM169_{SalI}$ | ΩTMV | control | 13 | 283 | — | — |
| $pFM191A_{SpeI}$ | ΩTMV | $TED_2$ | 90 | 1006 | 7 | 3.6 |
| $pFM169_{HindIII}$ | ΩTMV | control-$A_{100}$ | 26 | 3450 | — | — |
| $pFM209_{NheI}$ | ΩTMV | $TED_2$-$A_{100}$ | 102 | 3418 | 3.9 | 1.0 |

Control 3'UTR is a 120 nt plasmid derived sequence; translation stimulation has been normalized to the corresponding RNA construct without $TED_2$, for each case separately.

In the absence of both the cap and poly(A)-tail, $TED_2$ stimulates translation in vivo about 7-fold. When the RNA contained either a cap or a poly(A) tail, the stimulatory effect was about 4-fold. $TED_2$ did not increase translation of capped and polyadenylated cat RNA.

In vitro the STNV-2 leader and $TED_2$ cooperate to stimulate cap-independent translation. The different T7 RNA polymerase generated RNA transcripts comprising cat (summarized in Table 3), were introduced by electroporation in tobacco protoplasts. Samples for protein extraction were taken 6 hrs after RNA introduction, and the levels of CAT protein accumulated was determined. RNA level determination revealed that 90 min after electroporation the cat mRNA levels varied less than two-fold, indicating an RNA delivery with similar efficiency between the separate introduced RNAs. After 256 min, the cat mRNA levels were 3–5 fold lower in all experiments, indicating similar chemical half-lives for the different mRNAs.

TABLE 3

Cooperation between $TED_2$ and STNV-2 in vivo

| | Relevant features | | CAT level (pg/100 μg total protein) | |
|---|---|---|---|---|
| Template DNA | 5'UTR | 3'UTR | uncapped | capped |
| $pFM191_{SpeI}$ | STNV* | $TED_2$ | 10 | 185 |
| $pFM191E_{SpeI}$ | STNV-2 | $TED_2$ | 57 | 145 |
| $pFM189_{SalI}$ | STNV* | control | BB | ND |
| $pFM189A_{SalI}$ | STNV-2 | control | BB | ND |

ND = not determined; BB below background level (which is 2 pg); control refers to a 120 nt unrelated plasmid derived sequence CAT accumulation from uncapped RNAs was about five-fold higher in tobacco protoplasts expressing the STNV-25'UTR, than when a mutant 5'UTR of the similar length was used (STNV*). (A similar enhancement was observed in other independent experiments). Additionally, CAT protein accumulation profiles in tobacco protoplasts electroporated in the presence of uncapped $TED_2$ containing cat RNAs with the STNV* and the STNV-2 5'UTR were determined (Table 4). The STNV-2 leader fusion RNA encoded a higher peak level than the STNV* fusion RNA. The main difference between the profiles was that the initial rate of CAT accumulation was much greater for the STNV-2 leader fusion RNA than for the STNV* fusion RNA. This implies that the STNV-2 leader confers a higher translation efficiency to the RNA than the STNV* leader. To understand to what extent the observed difference in translation efficiency is related to intrinsic differences in the performance of the leaders, the profiles of both RNAs were compared to those of the capped RNAs C(able 4). The addition of a 5' cap had no effect on the functional half-lives of the RNAs but improved translation efficiency. Importantly, the addition of a 5' cap stimulated translation efficiency of the STNV-2 comprising RNA only 2.5 fold as opposed to 23-fold for the STNV* leader fusion RNA (see Table 4). This implies that the combined presence of the STNV-2 leader and $TED_2$ elements allows cap-independent translation to a level that is practically useful.

EXAMPLE 3

Determination of the Nucleotide Sequences From TNV sgRNA2 Leader and Trailer That Synergistically Stimulate Translation in Vitro and in Vivo As can be deduced from Table 5, TNV sgRNA2 contains translation enhancing sequences which allow uncapped TNV sgRNA2 to be translated in vitro to a coat protein peak level of 83% of the level obtained after in vitro translation of capped TNV sgRNA2.

TABLE 5

Effect of cap on translation of TNV sgRNA2 in vitro

| Template DNA[a] | cap | T.E. (cpm/min) | $t_{1/2}$ (min) | peak level (cpm) |
|---|---|---|---|---|
| pAB02(BsaI) | – | 318 ± 65 | 41 ± 17 | 18,800 |
| pAB02(BsaI) | + | 285 ± 45 | 55 ± 21 | 22,600 |

[a]RNAs were synthesized on the indicated plasmid DNA using T7 RNA polymerase. Samples were taken after 20, 30, 45, 60, 80, and 100 min of incubation at 25° C.

The elements of the TNV sgRNA2 that are required for an efficient translation were determined by comparison of translation of full-length TNV sgRNA2 with translation of deletion mutants in a wheat germ translation system.

RNAs were synthesized in vitro from the DNA templates summarized in Table 6, using T7 RNA polymerase. Translation of these RNAs, which differ in the presence or absence of the sgRNA25' UTR or 3' UTR sequences, was compared in a wheat germ translation system (Table 6). The indicated nucleotides remaining are the 31 nucleotides for the 5' UTR and the 5' nucleotides for the 3' UTR.

In the absence of the 5' UTR sequence, the 3' UTR increased the protein peak level only 1.5-fold, exclusively due to a longer functional half-life. The 5' UTR stimulated translation in the absence of the trailer about 3-fold. In the full-length sgRNA2, translation stimulation by the 5' UTR and 3' UTR (21- and 11-fold, respectively) is much higher than stimulation by the individual elements, indicating that the TNV sgRNA25' UTR and 3' UTR stimulate translation synergistically in vitro. The TNV sgRNA2 thus contains both a 5' and 3' translational enhancing sequence.

TABLE 4

Cooperation between STNV-2 leader and $TED_2$ in supporting cap-independent translation in tobacco protoplasts

| | Relevant features | | | T.E. (pg CAT/100 μg | $t_{1/2}$ | Peak level |
|---|---|---|---|---|---|---|
| Template DNA | 5'UTR | 3'UTR | 5' cap | protein.min) | (min) | (pg CAT/100 μg prot) |
| $pFM191_{SpeI}$ | STNV* | $TED_2$ | – | 0.26 ± 0.05 | 52.1 ± 10.2 | 19.54 |
| $pFM191_{SpeI}$ | STNV* | $TED_2$ | + | 6.13 ± 0.78 | 26.0 ± 3.5 | 229.94 |
| $pFM191E_{SpeI}$ | STNV-2 | $TED_2$ | – | 1.76 ± 0.88 | 24.6 ± 12.9 | 62.46 |
| $pFM191E_{SpeI}$ | STNV-2 | $TED_2$ | + | 4.52 ± 0.85 | 27.0 ± 5.5 | 176.07 |

TABLE 6

Effect of leader and trailer on translation of TNV SgRNA2 in vitro

| Template DNA | 5' UTR | 3' UTR | T.E. (cpm/min) | $t_{1/2}$ (min) | peak level (cpm) |
|---|---|---|---|---|---|
| pAB01(PCR1, *Afl*lll) | pl- 19 nt | 14 nt | 1.9 ± 0.4 | 14 ± 3 | 38 |
| pAB01(Bsal) | pl- 19 nt | 241 nt | 1.6 ± 0.3 | 26 ± 11 | 58 |
| pAB02(PCR1, *Afl*lll) | 152 nt | 14 nt | 4.0 ± 0.5 | 20 ± 4 | 115 |
| pAB02(Bsal) | 152 nt | 241 nt | 23.1 ± 2.4 | 37 ± 7 | 1218 |

pl refers to a 23 nucleotide long polylinker sequence.

The 3' border of the translation stimulating region in the trailer was determined by translation in a wheat germ extract of 3' deletion mutants of TNV sgRNA2 (Table 7). These mutant RNAs were synthesized in vitro using T7 RNA polymerase and pAB02 plasmid DNA that was linearized with different restriction enzymes. Translation of the RNA that lacks the 3'-terminal 73 nucleotides was comparable to that of the full-length sgRNA. Deletion of the next 49 nucleotides resulted in a two-fold decrease of translation. Further deletion of the trailer resulted in a further, gradual decrease in translation. These data allow to conclude that the 3' border of the second translation enhancing sequence lies between nucleotide 1102 and 1151 of sgRNA2.

TABLE 7

Determination of the 3' border of the 3' translation stimulating region of TNV sgRN2.

| Template DNA | 5' UTR | 3' UTR | T.E. (cpm/met/min) | $t_{1/2}$ (min) | peak level (cpm/met) | Relative peak level |
|---|---|---|---|---|---|---|
| pAB02(BsaI) | 152 nt | 241 nt | 98 ± 8 | 24 ± 3 | 3375 | 100 |
| pAB02(ApaLI) | 152 nt | 168 nt | 124 ± 8 | 21 ± 2 | 3795 | 112 |
| pAB02(BspEI) | 152 nt | 119 nt | 56 ± 7 | 23 ± 4 | 1824 | 54 |
| pAB02(BamHI) | 152 nt | 65 nt | 19.4 ± 1.4 | 27 ± 3 | 747 | 22 |
| pAB02(BsmAI) | 152 nt | 48 nt | 12.7 ± 1.2 | 32 ± 5 | 577 | 17 |
| pAB02(Bsu36I) | 152 nt | 31 nt | 4.0 ± 0.2 | 44 ± 4 | 253 | 7.5 |
| pAB02(PCR1, Af//III) | 152 nt | 14 nt | 8.4 ± 1.0 | 16 ± 2 | 190 | 5.6 |

To demonstrate that translation stimulation by the 3' stimulatory region is independent on its position relative to the translation stop codon, a new stop codon was created at nucleotide 735 of the TNV CP mRNA by filling-in and religating the EcoRI site of pAB02. The RNA specified by the resulting plasmid (pRD01) encodes a C-terminally truncated CP protein of 21-kDa. Translation of this RNA in the wheat germ extract was comparable to translation of the wild-type sgRNA2 (Table 8). This shows that the location of the translation termination site is not crucial for translation stimulation by the second translation enhancing sequence.

TABLE 8

Effect of the location of the translation termination codon on translation of TNV sgRNA2.

| Template DNA | translation termination site | T.E. (cpm/met/min) | $t_{1/2}$ (min) | peak level (cpm/met) | Relative peak level |
|---|---|---|---|---|---|
| pAB02(BsaI) | nt 981 | 226 ± 57 | 22 ± 9 | 7107 | 100 |
| pRD01(BsaI) | nt 734 | 210 ± 54 | 21 ± 8 | 6210 | 87 |

The 5' border of the second translation enhancing sequences from TNV-A was determined by comparison of the translation in vitro of the RNA comprising the newly introduced stop codon with translation of internal deletion mutants. RNAs were synthesized from the plasmids linearized with BsaI listed in Table 9, using T7 RNA polymerase, and translated in a wheat germ cell free extract. The data, summarized in Table 9, demonstrated that nucleotides 738 to 1011 of sgRNA2 could be deleted without affecting translation of the mutant RNA in vitro. Extension of this deletion to nucleotide 1044 caused a drop in translation of more than 10-fold, resulting in the same level of translation as for an RNA lacking the 3' UTR. Conclusively, the 5' border of the second translation enhancing sequence is located between nucleotides 1011 and 1044 of sgRNA2.

Moreover, the data also prove that the 5' and 3' translation stimulating regions are distinct domains, with the second translation enhancing sequence located between nucleotides 1011 and 1151 of sgRNA2.

TABLE 9

| Mapping of the 5' border of the 3' translation enhancing sequence of TNV sgRNA2 | | | | | |
|---|---|---|---|---|---|
| Template DNA | deletion (nt of sgRNA2) | T.E. (cpm/met/min) | $t_{1/2}$ (min) | peak level (cpm/met) | Relative peak level |
| pRD01(BsaI) | | 194 ± 15 | 15 ± 2 | 4198 | 100 |
| pRD02(BsaI) | 738–799 | 64 ± 5 | 46 ± 7 | 4247 | 102 |
| pRD06(BsaI) | 738–882 | 118 ± 14 | 32 ± 6 | 5448 | 130 |
| pRD03(BsaI) | 738–938 | 139 ± 8 | 24 ± 2 | 4813 | 115 |
| pRD04(BsaI) | 738–1011 | 183 ± 17 | 19 ± 2 | 5016 | 119 |
| pRD05(BsaI) | 738–1044 | 14.3 ± 2.6 | 20 ± 5 | 413 | 9.8 |
| pRD01(PCR1, Af//III) | 1030–1224 | 14.4 ± 1.8 | 18 ± 3 | 374 | 8.9 |

In vitro generated chimeric TNV-cat RNAs containing various parts of TNV 5' and 3' UTR flanking the cat coding region (Table 10) were introduced in tobacco protoplasts by electroporation to determine if 5'- and 3'-UTR of TNV sgRNA2 specify efficient translation of heterologous mRNAs in vivo.

The cat RNA levels in the transfected protoplasts were determined by quantitative Northern blot analysis to estimate the efficiency of RNA introduction. The results, summarized in Table 10, revealed that the efficiency of introduction of the TNV-cat RNAs varied less than two-fold.

Determination of the CAT protein levels (Table 10) revealed that the RNA which comprised only TNV 3' UTR specified low levels of CAT. The RNAs with both 5' and 3' UTR sequences from TNV directed the synthesis of levels of CAT which were 25- to 35-fold higher as compared to the RNA lacking TNV 5' UTR sequences. Similar levels of CAT protein resulted from the translation of the TNV-cat RNAs differing in the length of the 5' and 3' UTR sequence. Efficiency of uncapped RNA translation is only four fold lower than translation efficiency of capped RNA and only two-fold lower than for a very efficiently translated mRNA (pFM169HindIII).

These data demonstrate that first and second translation enhancing sequences from TNV sg RNA2 allow efficient cap-independent translation in vivo.

TABLE 10

| Translation of chimeric TNV-cat RNAs in tobacco protoplasts[a] | | | | |
|---|---|---|---|---|
| Template DNA | leader | trailer | cat RNA level | CAT protein level |
| $pFM188I_{BsaI}$ | us(19) | us(112)/883–1224 | 35 | 182 ± 4 |
| $pFM188H_{BsaI}$ | 1-138 | us(112)/883–1224 | 28 | 4730 ± 540 |
| $pFM188C_{BsaI}$ | 1-138 | us(22)/939–1224 | 20 | 6310 ± 10 |
| $pFM188G_{BsaI}$ | 1-159 | us(112)/883–1224 | 29 | 5300 ± 220 |
| $pFM188G_{BsaI}$ | CAP-1-159 | us(112)/883–1224 | 29 | 21200 ± 2500 |
| $pFM169_{HindIII}$ | CAP-Ω | us(140)/$A_{100}$ | 8 | 47800 |

[a]RNA was synthesized on the indicated plasmid DNAs using T7 RNA polymerase and introduced in tobacco protoplasts by electroporation. The composition of the leader and trailer sequences is given, using the nucleotide numbering of the TNVsgRNA2; us = unrelated sequence with the length indicated in nucleotides;. Total RNA was isolated from the protoplasts 140 min after electroporation. The cat RNA levels are in amol/μg of total RNA. The CAT protein level (pg/mg of soluble protein) wasdetermined 340 min after RNA introduction, in duplo.

RNA was synthesized, using T3 RNA polymerase from BsaI-, and ApaLI-digested pVE190, pVE195 and pVE196 and from Bsu36I-digested pVE190 and pVE195. These RNAs were introduced into tobacco protoplasts. CAT accumulation was monitored, at least 5 hours after RNA introduction. This revealed that the minimal 3' TNV sequences required for an efficient translation of an uncapped cat mRNA are located between nt 1012 and 1151 of TNV-A sgRNA2 (see Table 10 bis).

TABLE 10 bis

Translation of chimeric TNV-cat RNAs in tobacco protoplasts[a]

| | leader | trailer | cat RNA level | CAT protein level |
|---|---|---|---|---|
| pVE190 BsaI | 1-138 | us(22)/939–1224 | 2.23 | 39.5 +/− 7.6 |
| pVE190 Bsu36I | 1-138 | us(22)/939–1014 | 2.03 | 0 |
| pVE195 BsaI | 1-143/caaaacc | gctagc/969–1224 | 1.85 | 45.0 +/− 5.3 |
| pVEI95 Bsu36I | 1-143/caaaacc | gctagc/969–1014 | 2.21 | 0 |
| pVE196 BsaI | 1-143/caaaacc | gctagc/1012–1224 | 1.20 | 41.7 +/− 3.3 |
| pVE196 ApaLI | 1-143/caaaacc | gctagc/1012–1151 | 0.86 | 37.5 +/− 8.4 |

[a]RNA was syntesized on the indicated plasmid DNAs using T7 RNA polymerase and introduced in tobacco protoplasts by electroporation. The composition of the leader and trailer sequences is given, using the nucleotide numbering of TNVsgRNA2; us = unrelated sequecne with the length indicated in nucleotides. Total RNA was isolated from the protoplasts 130 min after elctroporation. The cat RNA levels are in amol/μg of total RNA. The CAT protein level (pg/40 μg soluble protein) wasdetermined 5 hours after RNA introduction, in duplo.

An infective TNV-A RNA wherein the CP coding region was replaced by the cat coding region, was synthesized in vitro from BsaI-digested pFM216 DNA and introduced in tobacco protoplasts, by electroporation. As a control, a cat RNA containing STNV-2 leader and trailer (generated by in vitro transcription of AvaI-linearized pFM207E), was introduced together with TNV RNA in tobacco protoplasts. Two days after infection, cat RNA and protein accumulation was monitored. As indicated in Table 11, the ratio protein/RNA was about 40 times higher for the TNV-cat RNA than for the STNV-cat RNA.

TABLE 11

Comparison of cap-independent translation of replicating RNAs

| | RNA (fmol/μg tot RNA) | CAT protein (μg/mg sol. protein) | Ratio CAT/RNA | Relative ratio CAT/RNA |
|---|---|---|---|---|
| TNV-cat | 1 | 16 | 1.6 | 44 |
| STNV-cat | 66 | 24 | 0.036 | 1 |

EXAMPLE 4

Effect of Codon Sequence on in Vivo Translation in Tobacco Protoplasts

In vitro generated RNA transcripts comprising first and second translation enhancing sequences from STNV-2, using as templates the DNA listed in Table 12, were introduced in tobacco protoplasts by electroporation (together with TNV RNA to supply the RNA-dependent RNA polymerase in trans). These transcripts contain either native or synthetic coding regions of a Bt ICP gene. After 48 hrs, the amount of synthesized protein and positive-strand RNA was determined. Table 12 summarizes the ratios of synthesized protein over synthesized RNA (normalized to the value obtained for native coding sequence).

TABLE 12

Protein/(+) RNA ratio obtained 48 hrs after RNA introduction in tobacco protoplasts.

| Used template for in vitro RNA generation | Coding Region | Protein/(+) RNA | Normalized protein/(+)RNA |
|---|---|---|---|
| pRVL11(BsaI-linearized) | [$cry9C_{native}$] | 0.27 | 1 |
| pRVL12(BsaI-linearized) | [$cry9C_{synth}$] | 0.1 | 0.37 |

The ratio of accumulated protein/accumulated RNA after 48 hrs was higher when native coding sequences were utilized than when synthetic coding regions, with codon preferences closer to that of plants, were used.

After introduction of the cry9C transcripts in tobacco protoplasts (both native and synthetic coding sequences), an in vivo RNA and protein accumulation profile was determined, wich allows to estimate the ratio of the translation efficiency for both types of RNA (Table 13). Again, a higher translation enhancing activityy was obtained for the native coding sequence.

TABLE 13

CRY9C protein and uncapped RNA accumulation in tobacco protoplasts.

| Used template for in vitro RNA generation | Coding Region | uncapped RNA accumulation | Protein accumulation | (dP/dt)/(dR/dt) | Normalized translation efficiency |
|---|---|---|---|---|---|
| pRVL11(BsaI-linearized) | [cry9$C_{wt}$] | R = 0.07t − 0.1 | P = 2.3t − 23 | 32.9 | 1 |
| pRVL12(BsaI-linearized) | [cry9$C_{synth}$] | R = 0.13t − 0.3 | P = 2.1t − 35 | 16.2 | 0.49 |

R=RNA (fmole/0.5 μg total RNA); P=protein (ng/mg soluble protein); t=time(hours)

EXAMPLE 5

$TED_2$ Stimulates Autonomously the Translation of Dicistronic RNAs in Vitro Efficient cap-independent translation of both cistrons of a dicistronic RNA by TED from STNV-2, as present in plasmids pFM203 and PFM203B was ascertained as follows.

Construction of pFM203 and PFM203B was based on pMA442, which is an in vitro transcription plasmid containing the nptil coding region between the first 173 nucleotides and the trailer of the STNV-2 RNA. It consists of the following sequences: from nucleotide 1 to 1003 it has the nucleotide sequence of SEQ ID No.38; from nucleotide 1004–1616 it has the nucleotide sequence between 633 and 1245 of SEQ ID No. 2; from nucleotide 1617 to 1633 it corresponds to nucleotide 24 to 40 of pGEM®-3Z; from nucleotide 1634 to 1698 it contains nucleotides 2499 to 2435 of pGEM®-1 (in counterclockwise orientation) and from nucleotide 1699 to 4173 it corresponds to nucleotide 269 to 2743 of pGEM®-3Z. pFM203 was obtained by cloning of the 1246-bp long XhoI-NsiI fragment of pMA442 between the SalI and PstI sites of pFM189. To construct pFM203B, the NsiI-blunted-Asp7181 1077 bp fragment of pMA442 was first cloned between the PstI and blunted XbaI sites of pFM189, resulting in pFM21 IA. Religation of blunted NcoI-EcoRI-digested pXD324 DNA resulted in pFM170D. To obtain pFM170, the nptII coding region was inserted as an EcoRI-BstBI fragment (SEQ ID No. 39 between the nucleotides at position 3 and 818) between the EcoRI and AccI sites of pFM170D. A 260-nt-long PstI-filled-in-BamHI fragment of pFM170 was inserted between the PstI and trimmed KpnI sites of pFM211A, resulting in plasmid pFM203B. In general the structure of the relevant features pFM203 and pFM203B can be represented as follows:

pFM203:T7-STNV*leader-cat-STNV2(1-173)nptII (transl.fusion)-TED pFM203B: T7-STNV*leader-cat-TMVleader-nptII-TED In vitro transcription with T7 RNA polymerase of BspHI- or SpeI-digested plasmid pFM203 or pFM203B DNA resulted in the synthesis of dicistronic RNAs lacking or including TED, respectively. Capped and uncapped RNA transcripts were translated in vitro in a wheat germ extract. Protein accumulation profiles were determined and translation efficiencies as well as functional half-lives were deduced, allowing calculation of the peak levels.

The results summarized in Table 14 show that $TED_2$ stimulates cap-independent translation of both cistrons to the same extent. Translation of the second cistron is by internal initiation as it is hardly stimulated by a cap and not proportional to the level of translation of the first cistron.

TABLE 14

$TED_2$ stimulates autonomously the translation of dicistronic RNAs in vitro.

| | | CAT | | | NPTII | | |
|---|---|---|---|---|---|---|---|
| Plasmid | cap | T.E. (Relative units) | t½ (min) | Peak level | T.E. | t½ (min) | Peak level |
| pFM203 BspHI | no | 2.8 ± 0.3 | 19.8 ± 2.3 | 79.7 | 1.26 ± 0.18 | 31.4 ± 6.8 | 57.1 |
| pFM203 SpeI | no | 71.1 ± 9.2 | 6.1 ± 0.9 | 626 | 23.1 ± 1.7 | 13.0 ± 1.2 | 433 |
| pFM203B BspHI | no | 1.21 ± 0.16 | 10.5 ± 1.7 | 18.3 | 0.58 ± 0.10 | 20.5 ± 5.7 | 17.2 |
| pFM203B BspHI | yes | 12.2 ± 1.1 | 24.6 ± 3.6 | 433 | 1.00 ± 0.40 | 14.9 ± 7.7 | 21.5 |
| pFM203B SpeI | no | 19.6 ± 3.4 | 13.4 ± 2.9 | 379 | 6.35 ± 0.91 | 32.3 ± 9.4 | 296 |
| pFM203B SpeI | yes | 24.1 ± 2.6 | 43.2 ± 10.3 | 1502 | 5.26 ± 0.14 | 73.5 ± 6.9 | 558 |

EXAMPLE 6

Construction of Plant Transformation Vectors

Below, the different steps to construct the interchangeable cassettes for the build-up of the plant transformation vectors are transcribed. These cassettes, which are ultimatily under the control of a T3 or T7 promoter, comprise: (i) a terminator sequence for T3 and T7 RNA polymerases,(ii) Bt ICP encoding genes, flanked by appropriate DNA regions encoding the first and second translation enhancing sequences of TNV-A or STNV-2, (iii) marker genes which are either under the control of a plant-expressible promoter, or are under control of T3 or T7 promoters and are further flanked by appropriate DNA regions encoding first and second translation enhancing sequences of TNV-A or STNV-2, and (iv) a T3 or T7 RNA polymerase encoding gene under control of a plant-expressible promoter, whereby the RNA polymerase is joined to a nuclear localization signal of SV40 T-antigen.

Several combinations of these cassettes are made, yielding the plasmids of the pFM-series summarized in Table 15. Other combinations were made yielding the plasmids of the pVE-series summarized in Table 15. In these plasmids, the combined cassettes are flanked by unique restriction sites for the octacutters Sse83871 and SgfI, hence they can be excised as one fragment and introduced in the polylinker sequence between the T-DNA borders of the T-DNA vector pTFM600, to yield the plant transformation vectors of pTFM-series summarized in Table 15. Alternatively, the combined cassettes flanked by unique restriction sites for the octacutters Sse83871 and SgfI, were excised as one fragment and introduced in the polylinker sequence between the T-DNA borders of the T-DNA vector pGVS20 to yield the plant transformation vectors of pTVE-series summarized in Table 15.

(i) Construction of DNA cassette comprising terminator sequences for T3 and T7 RNA polymerases.

A synthetic DNA fragment comprising the T3 terminator sequence, flanked by unique restriction sites (nucleotide sequence of in SEQ ID No.24) was cloned as a PstI-HindIII downstream of the TNV trailer, between the PstI and HindIII sites of pVE190 (see Example 1), resulting in plasmid pVE198. The terminator fragment was then duplicated by ligating the terminator-containing EcoRI-XbaI and EcoRI-SpeI fragments of pVE198 or the terminator-containing NdeI-XbaI and NdeI-SpeI fragments, resulting in plasmid pVE199. The duplicated terminator fragment of pVE199 was fused to the ApaLI site of the TNV trailer by cloning of the 631-bp ApaLI(blunted)-EcoRI fragment of pVE195 (see Example 1) between the EcoRI and trimmed PstI sites of pVE199, yielding plasmid pFM500.

(ii) Construction of the DNA cassettes comprising Bt ICP encoding genes flanked by appropriate DNA regions complementary to the leader and (portions of the) trailer of STNV-2 or TNV-A.

a. Bt ICP encoding genes flanked by STNV-2 sequences.

A fragment was amplified by PCR on plasmid pRVL11 (see Example 1) with primers FM22 and FM25 having the nucleotide sequences of SEQ ID No.30 and SEQ ID No.31, digested with HindIII and NdeI, and cloned between the HindIII and NdeI sites of pRVL11, resulting in plasmid pRVL17. The cry9C-containing NdeI-SpeI fragment of pRVL17 was cloned between the NdeI and SpeI sites of pFM500, resulting in plasmid pFM407.

The cry1A(b)-containing NcoI-NheI fragment of pGEM1Ab1 (see example 1)is fused to the 310-bp AatII-NcoI and the 2554-bp NheI-AatII fragments of pFM407, resulting in plasmid pFM408.

b. Bt ICP encoding genes flanked by TNV-A sequences.

A PCR fragment is was amplified with primers FM22 and FM6 having the nucleotide sequence of SEQ ID No.30 and SEQ ID No.29 using plasmid pAB02 (see Example 1) as a template, digested with NheI and NdeI and cloned between the NheI and NdeI sites of pFM500, resulting in plasmid pFM401.

A PCR fragment was amplified with primers FM26 and FM6 having the nucleotide sequence of SEQ ID No.32 and SEQ ID No.29 using plasmid pVE190 (see example 1) as a template, digested with NheI and NdeI and cloned between the NheI and NdeI sites of pFM500, resulting in plasmid pFM501.

The cry9C-containing NcoI-NheI fragment of pGEM9C1 (see example 1) was cloned between the NcoI and NheI sites of pFM401, resulting in pFM402. pFM402 is then digested with NheI and Bsu36I, blunted and ligated, resulting in plasmid pFM403.

The cry1A(b)-containing is cloned between the NcoI and NheI sites of pFM401, resulting in pFM404.

The cry-containing NcoI-EagI fragments of pFM402, pFM403, and pFM404 are then cloned between the NcoI and EagI sites of pFM501, resulting in plasmids pFM502, pFM503, and pFM504, respectively. In an alternative way, plasmids pFM502 and pFM504 were constructed by cloning the NcoI-NheI fragment of pGEM9C1, respectively the NcoI-NheI fragment of pGEM1Ab1 in NcoI-NheI digested pFM501.

(iii) Marker gene cassettes.

As a source for the conventional marker gene (chimeric 35S-bar gene) we used plasmid pDE110. Plasmid pDE110 is a pUC-derivative containing the bar coding region under the control of the 35S promoter and the 31 end formation signal of Cauliflower mosaic virus. It comprises the followings fragments: from nucleotide 1 to nucleotide 401 it equals nucleotide 1 to nucleotide 401 of pUC19 (Yanisch-Perron et al., 1985); from nucleotide 402 to nucleotide 1779 it comprises a promoter region of the Cauliflower mosaic virus 35S RNA (Odell et al. Nature 313, 810–812 (1985); from nucleotide 1781 to nucleotide 2332 it comprises the coding region of the bialaphos resistance (bar) gene from *Streptomyces hygroscopicus* (Thompson et al., 1987); from nucleotide 2351–2614 it comprises a fragment containing the 3'-end formation signal of the nopaline synthase gene from the T-DNA of pTiT37 (Depicker et al., 1982); and from nucleotide 2615 to nucleotide 4883 it equals nucleotide 418 to nucleotide 2686 of pUC19.

To obtain a DNA cassette comprising the bar gene flanked by DNA encoding the first and second translation enhancing sequences from TNV-A, under control of T3 or T7 promoters, the bar-gene containing NcoI-filled-in-MluI fragment of pFM133 (see Example 1) was cloned between the NcoI and filled-in NheI sites of pFM401 and pFM501, resulting in plasmids pFM405 (T7-promoter) and pFM505 (T3-promoter), respectively.

To obtain a DNA cassette comprising the bar gene flanked by DNA encoding the first and second tranlation enhancing sequences from STNV-2, under control of T7 promoter, the bar-gene containing NheI-NcoI fragment of pFM405 is fused to the 310-bp AatII-NcoI fragment and the 2554-bp NheI-AatII fragment of pFM407, resulting in plasmid pFM406. In an alternative way, plasmid pFM406 was obtained by fusing the the bar-gene containing NheI-NcoI fragment of pFM405 to the 1.2 kb Bgil-NcoI fragment and the 1.8 kb NheI-BgIn fragment of pFM407.

(iv) Construction of DNA cassettes encoding T3 or 17 RNA polymerase under control of plant-expressible promoter.

The T7 RNA polymerase coding region is present on a DNA fragment which has the following sequence: from nucleotide 1 to 35: the nucleotide sequence as in SEQ ID No.36 (comprising the coding sequence for the nuclear localisation signal of the SV40 large T-antigen); from nucleotide 36 to nucleotide 2684: the sequence of Genbank Accession No. V01146 (incorporated herein by reference) between the nucleotide at position 3174 and the nucleotide at position 5822 comprising the T7 RNA polymerase coding region; from nucleotide 2685 to nucleotide 2690: GCTAGC. The T3 RNA polymerase coding region is comprised within a similar DNA fragment in which the sequence between the nucleotide at position 36 and the nucleotide at position 2684 are replaced with the sequence of Genbank Accession No. X02981 (incorporated herein by reference) between the nucleotide at position 144 and the nucleotide at position 2795. Such fragments can be obtained by PCR using appropriate primers and plasmids pAR1173 (ATCC 39562) or the T7 genome; and plasmid pCM56 (ATCC 53202) or the T3 genome.

pFM409 is a pUC19-derivative containing four unique 8-base cutters (Sse83871, AscI, NotI, SgfI), wherein between the Sse83871 and AscI sites a gene cassette is inserted which consists of: a CaMV35S promoter, the leader sequence of the cab22L gene from Petunia, the 5' region of the cry1A(b)5 coding region and a 3'-end formation signal of CaMV. It has the following sequence: from nucleotide 1 to nucleotide 186 it equals the nucleotide sequence of pUC19 from nucleotide position 1 to nucleotide position 186; from nucleotide position 187 to nucleotide position 1220 it has the nucleotide sequence of SEQ ID No.35; from nucleotide position 1221 to nucleotide position 3460 it has the nucleotide sequence of pUC19 between the nucleotides at position 447 and 2686 of pUC19.

The T7 RNA polymerase coding region is placed under the control of a 35S promoter of CaMV by cloning as a NcoI-NheI fragment of the above mentioned DNA between the NcoI and NheI sites of pFM409, resulting in plasmid pFM410.

Similarly, the T3 RNA polymerase coding region is cloned as an NcoI-NheI fragment of the above mentioned DNA between the NcoI and NheI sites of pFM409, resulting in plasmid pFM510.

(V) Assembly of the plant transformation vectors.

The major plasmids, used for the assembly of the plant transformation vectors have the following schematized structure:

pFM402: T7p-TNVleader-cry9C-TNVtrailer(1)-T3term(2x)
pFM403: T7p-TNVleader-cry9C-TNVtrailer(2)-T3term(2x)
pFM404: T7p-TNVleader-cry1Ab5-TNVtrailer(1)-T3term (x2)
pFM502: T3p-TNVleader-cry9C-TNVtrailer(1)-T3term(2x)
pFM503: T3p-TNVleader-cry9C-TNVtrailer(2)-T3term(2x)
pFM504: T3p-TNVleader-cry1Ab5-TNVtrailer(1)-T3term (2x)
pFM405: T7p-TNVleader-bar-TNVtrailer(1)-T3term(2x)
pFM505: T3p-TNVleader-bar-TNVtrailer(1)-T3term(2x)
pFM406: T7p-STNVleader-bar-TED-T3term(2x)
pFM407: T7p-STNVleader-cry9C-TED-T3term(2x)
pFM408: T7p-STNVleader-cry1Ab5-TED-T3term(2x)
pFM410: P35S-cab22leader-T7pol-3'35S
pFM510: P35S-cab22leader-T3pol-3'35S
pDE 10: P35S-bar-3'nos.

The DNA encoding the translation enhancing sequence indicated as TNV trailer (1) has the sequence of SEQ ID No.1 between the the nucleotides at position 3429 and 3611; the one indicated as TNV trailer (2) has the sequence of SEQ ID No.1 between the nucleotides 3472 and 3611. TED refers to the DNA encoding a STNV second translation enhancing sequence corresponding to SEQ ID No.2 between nucleotides at position 632 and 753; P35S refers to a CaMV35S promoter; TNV leader refers to the DNA encoding first translation enhancing sequence corresponding to the nucleotide sequence of SEQ ID No.1 between the nucleotides at positions 2461 and 2603; STNV leader refers to the DNA encoding a first translation enhancing sequence corresponding to SEQ ID No. 2 between nucleotides at position 1 and 38; cab22L leader refers to the DNA sequence encoding the leader sequence from cab22L gene of Petunia, having the nucleotide sequence complementary to the nucleotide sequence of SEQ ID No. 35 between nucleotides at positions 370 and 429; T7p refers to the T7 promoter having the sequence of SEQ ID No.30 between nucleotides 22 and 39; T3p refers to the T3 promoter having the sequence of SEQ ID No.18 between nucleotides 14 and 32; 3' nos and 3' 35S refer to the 3' region of the nopaline synthase gene and the CaMV 35S transcript (having the complementary nucleotide sequence of SEQ ID No. between nucleotide 27 and 249), respectively; T3 term refers to the terminator region of phage T3 having the nucleotide sequence of SEQ ID No.24; cry 9C refers to the native nucleotide sequence encoding a truncated toxic fragment of CRY9C as indicated in SEQ ID No. 5 between nucleotide positions 6 and 1892; cry 1A(b) refers to the native nucleotide sequence encoding a truncated toxic fragment of CRY1Ab5 as indicated in SEQ ID No. 6 between nucleotide positions 8 and 1783.

pTFM600 was derived from plasmid pGSC1700 [Comelissen and Vandewiele (1989), *Nucl. Acids Res.* 17: 833] but differs from the latter in that it does not contain a beta-lactamase gene and that its T-DNA is characterized by the sequence of SEQ ID No.37.

PGVS20 was derived from pTFM600 by removal of the SphI site, followed by introduction of a DNA fragment derived from the nptI gene (Genbank Accesion No. V00359 between nucleotides 787 and 2308 wherein nucleotides 1592 and 1593 were removed) in the vector-part outside the T-DNA region, using standard recombinant DNA procedures.

The chimeric bar gene under control of a CaMV35S promoter is cloned as a StuI-XbaI fragment of pDE110 between the HpaI site and the XbaI site of pFM410 (containing the chimeric T7 RNA polymerase gene) and pFM510 (containing the chimeric T3 RNA polymerase gene), resulting in plasmids pFM411 and pFM511, respectively.

The chimeric bar gene under control of a T7 promoter is cloned as a BssHII-XbaI fragment of pFM405 (flanked by TNV-A sequences) or pFM406 (flanked by STNV-2 sequences) between the MluI and XbaI sites of pFM410, resulting in plasmids pFM412 and pFM413, respectively.

The chimeric bar gene under control of a T3 promoter is cloned as a BssHII-XbaI fragment of pFM505 (flanked by TNV-A sequences) between the MluI and XbaI sites of pFM510, resulting in plasmid pFM512.

The chimeric cry genes under control of a T7 promoter of pFM402, pFM403, pFM404, pFM407, or pFM408 are cloned as BssHII-EagI fragments between the Asci and NotI sites of pFM411, pFM412, or pFM413 to obtain the plasmids pFM414-pFM422 of Table 15.

The chimeric cry genes under control of a T3-specific promoter of pFM502, pFM503, and pFM504 are cloned as BssHII-EagI fragments between the AscI and NotI sites of pFM511 and pFM512.

Finally the Sse83871-SgfI fragments of pFM411 to pFM422, and of pFM511 to pFM520 are cloned between the Sse83871 and SgfI sites of the T-DNA vector pTFM600, to yield the T-DNA vectors of the pTFM-series summarized in Table 15.

Using standard cloning procedures, the plasmids pVE220 (analogous to pFM414), pVE221 (analogous to pFM419), pVE222 (analogous to pFM417), pVE223 (analogous to pFM514) and pVE224 (analogous to pFM519) were made.

pVE220 comprises the following nucleotide sequence: from nucleotide 1 to 186: the sequence from the nucleotide at position 1 to the nucleotide at position 186 of pUC19; from nucleotide 187 to 201: the sequence from the nucleotide at position 1 to the nucleotide at position 15 of SEQ ID No. 35; from nucleotide 202 to 207: CCGCTG; from nucleotide 208 to 453: the sequence from the nucleotide at position 16 to the nucleotide at position 261 of SEQ ID No. 35, the complementary sequence of which comprises the 3' end formation signal of cauliflower mosaic virus; from nucleotide 454 to 3102: the sequence complementary to Genbank Accession No. V01146 from the nucleotide at position 3174 to the nucleotide at position 5822, which comprises the T7 RNA polymerase coding region; from nucleotide 3103 to 3137: the sequence complementary to the sequence from the nucleotide at position 35 to the nucleotide at position 1 of SEQ ID No. 36, which comprises the coding sequence for the nuclear localization signal of the SV40 large T-antigen; from nucleotide 3138 to 3736: the sequence from the nucleotide at position 372 to the nucleotide at position 970 of SEQ ID No. 35, the complementary sequence of which comprises the cab22L leader sequence and a promoter of the cauliflower mosaic virus 35S RNA; from nucleotide 3737 to 3738: AT; from nucleotide 3739 to 3752: the sequence from the nucleotide at position 971 to the nucleotide at position 984 of SEQ ID No. 35; from nucleotide 3753 to 3776: the sequence from the nucleotide at position 15 to the nucleotide at position 38 of SEQ ID No. 30, comprising the T7 RNA polymerase promoter; from nucleotide 3777 to 3919: the sequence from the nucleotide at position 2461 to the nucleotide at position 2603 of SEQ ID No.1, comprising a first translation enhancing sequence of TNV; from nucleotide 3920 to 5811: the sequence from the nucleotide at position 6 to the nucleotide at position 1897 of SEQ ID No. 5, comprising the cry9C coding region; from nucleotide 5812 to 5994: the sequence from the nucleotide at position 3429 to the nucleotide at position 3611 of SEQ ID No. 1, comprising a second translation enhancing sequence of TNV; from nucleotide 5995 to 6109: the sequence from the nucleotide at position 6 to the nucleotide at position 120 of SEQ ID No. 24, comprising the T3 RNA polymerase terminator sequence; from nucleotide 6110 to 6222: the sequence from the nucleotide at position 16 to the nucleotide at position 128 of SEQ ID No. 24, comprising the T3 RNA polymerase terminator sequence; from nucleotide 6223 to 6244: the sequence from the nucleotide at position 988 to the nucleotide at position 1009 of SEQ ID No. 35; from nucleotide 6245 to 7918: the sequence from the nucleotide at position 947 to the nucleotide at position 2620 of PDE110 (StuI-XbaI fragment), comprising the bar coding region under the control of a promoter and a 3' end formation signal of the cauliflower mosaic virus; from nucleotide 7919 to 7931: the sequence from the nucleotide at position 1022 to the nucleotide at position 1034 of SEQ ID No. 35; from nucleotide 7932 to 10171: the sequence from the nucleotide at position 447 to the nucleotide at position 2686 of pUC19.

Plasmid pVE221 comprises the following nucleotide sequence: from nucleotide 1 to 6244: the sequence from the nucleotide at position 1 to the nucleotide at position 6244 of pVE220; from nucleotide 6245 to 6247: AAC; from nucleotide 6245 to 6271: the sequence from the nucleotide at position 15 to the nucleotide at position 38 of SEQ ID No. 30, comprising the T7 RNA polymerase promoter; from nucleotide 6272 to 6414: the sequence from the nucleotide at position 2461 to 2603 the nucleotide at position of SEQ ID No. 1, comprising a first translation enhancing sequence of TNV; from nucleotide 6415 to 6421: the sequence from the nucleotide at position 6 to the nucleotide at position 12 of SEQ ID No. 5; from nucleotide 6422 to 6982: the sequence from the nucleotide at position 1780 to the nucleotide at position 2340 of pDE110, comprising the bar coding region; from nucleotide 6983 to 6987: CTAGC; from nucleotide 6988 to 7170: the sequence from the nucleotide at position 3429 to the nucleotide at position 3611 of SEQ ID No. 1, comprising a second translation enhancing sequence of TNV; from nucleotide 7171 to 7285: the sequence from the nucleotide at position 6 to the nucleotide at position 120 of SEQ ID No. 24, comprising the T3 RNA polymerase terminator sequence; from nucleotide 7286 to 7389: the sequence from the nucleotide at position 16 to the nucleotide at position 119 of SEQ ID No. 24, comprising the T3 RNA polymerase terminator sequence; from nucleotide 7390 to 9642: the sequence from the nucleotide at position 7919 to the nucleotide at position 10171 of pVE220.

Plasmid pVE222 comprises the following nucleotide sequence: from nucleotide 1 to 3919: the sequence from the nucleotide at position 1 to the nucleotide at position 3919 of pVE220; from nucleotide 3920 to 5706: the sequence from the nucleotide at position 2 to the nucleotide at position 1788 of SEQ ID No. 6 comprising the cry1Ab5 coding region; from nucleotide 5707 to 10066: the sequence from the nucleotide at position 5812 to the nucletide at position 10171 of pVE220.

Plasmid pVE223 comprises the following nucleotide sequence: from nucleotide 1 to 453: the sequence from the nucleotide at position 1 to the nucleotide at position 453 of pVE220; from nucleotide 454 to 3105: the sequence complementary to Genbank Accession No. X02981 from the nucleotide at position 144 to the nucleotide at position 2795, comprising the T3 RNA polymerase coding region; from nucleotide 3106 to 3755: the sequence from the nucleotide at position 3103 to the nucleotide at position 3752 of pVE220; from nucleotide 3756 to 3760: the sequence from the nucleotide at position 15 to the nucleotide at position 19 of SEQ ID No. 30; from nucleotide 3761 to 3780: the sequence from the nucleotide at position 12 to the nucleotide at position 31 of SEQ ID No. 18, comprising the T3 RNA polymerase promoter; from nucleotide 3781 to 10175: the sequence from the nucleotide at position 3777 to the nucleotide at position 10171 of pVE220.

Plasmid pVE224 comprises the following nucleotide sequence: from nucleotide 1 to 6226: the sequence from the nucleotide at position 1 to the nucleotide at position 6226 of pVE220; from nucleotide 6227 to 6250: the sequence from the nucleotide at position 988 to the nucleotide at position 1011 of SEQ ID No. 35; from nucleotide 6251 to 6256: the sequence from the nucleotide at position 14 to the nucleotide at position 19 of SEQ ID No. 30; from nucleotide 6257 to 6276: the sequence from the nucleotide at position 12 to the nucleotide at position 31 of SEQ ID No. 18, comprising the T3 RNA polymerase promoter; from nucleotide 6277 to 9647: the sequence from the nucleotide at position 6272 to the nucleotide at position 9642 of pVE221.

pVE236 is a plasmid analogous to pVE220 wherein the additional nucleotides of the T7 consensus promoter are incorporated. The plasmid has the sequence of pVE220, but for the insertion of the nucleotide sequence GGAG between nucleotide position 3777 and 3778 of pVE220.

Finally the Sse83871-SgfI fragments of pVE220, pVE221, pVE222, pVE223, pVE224 were cloned between the Sse83871 and SgfI sites of the T-DNA vector pGSV20, to yield the T-DNA vectors of the pTVE-series summarized in Table 15.

TABLE 15

Summary of the plant transformation vectors.

| Plasmid | T-DNA vector | Promoter | Leader | coding region | trailer | terminator | RNA polymerase | selectable marker |
|---|---|---|---|---|---|---|---|---|
| pFM411 | pTFM411 | — | — | — | — | — | T7 RNA Pol | P35S-bar |
| pFM412 | pTFM412 | — | — | — | — | — | T7 RNA Pol | T7-TNV-bar |
| pFM413 | pTFM413 | — | — | — | — | — | T7 RNA Pol | T7-STNV-bar |
| pFM414 | pTFM414 | T7 | TNVsgPNA2 | cry9C | TNV (1) | T3 | T7 RNA Pol | P35S-bar |
| pVE220 | pTVE228 | T7 | TNVsgPNA2 | cry9C | TNV (1) | T3 | T7 RNA Pol | P35S-bar |
| pFM415 | pTFM415 | T7 | TNVsgRNA2 | cry9C | TNV (2) | T3 | T7 RNA Pol | P35S-bar |
| pFM416 | pTFM416 | T7 | STNV | cry9C | TED | T3 | T7 RNA Pol | P35S-bar |
| pFM417 | pTFM417 | T7 | TNVsgRNA2 | cry1A(b) | TNV (1) | T3 | T7 RNA Pol | P35S-bar |
| pVE222 | pTVE230 | T7 | TNVsgRNA2 | cry1A(b) | TNV (1) | T3 | T7 RNA Pol | P35S-bar |
| pFM418 | pTFM418 | T7 | STNV | cry1A(b) | TED | T3 | T7 RNA Pol | P35S-bar |
| pFM419 | pTFM419 | T7 | TNVsgPNA2 | cry9C | TNV (1) | T3 | T7 RNA Pol | T7-TNV-bar |
| pVE221 | pTVE229 | T7 | TNVsgRNA2 | cry9C | TNV (1) | T3 | T7 RNA Pol | T7-TNV-bar |
| pFM420 | pTFM420 | T7 | TNVsgRNA2 | cry9C | TNV (2) | T3 | T7 RNA Pol | T7-TNV-bar |
| pFM421 | pTFM421 | T7 | TNVsgRNA2 | cry9C | TNV (1) | T3 | T7 RNA Pol | T7-STNV-bar |
| pFM422 | pTFM422 | T7 | TNVsgRNA2 | cry9C | TNV (2) | T3 | T7 RNA Pol | T7-STNV-bar |
| pFM511 | pTFM511 | — | — | — | — | — | T3 RNA Pol | P35S-bar |
| pFM512 | pTFM512 | — | — | — | — | — | T3 RNA Pol | T3-TNV-bar |
| pFM514 | pTFM514 | T3 | TNVsgRNA2 | cry9C | TNV (1) | T3 | T3 RNA Pol | P35S-bar |
| pVE223 | pTVE225 | T3 | TNVsgRNA2 | cry9C | TNV (1) | T3 | T3 RNA Pol | P35S-bar |
| pFM515 | pTFM515 | T3 | TNVsfRNA2 | cry9C | TNV (2) | T3 | T3 RNA Pol | P35S-bar |
| pFM517 | pTFM517 | T3 | TNVsgRNA2 | cry1A(b) | TNV (1) | T3 | T3 RNA Pol | P35S-bar |
| pFM519 | pTFM519 | T3 | TNVsgRNA2 | cry9C | TNV (1) | T3 | T3 RNA Pol | T3-TNV-bar |
| pVE224 | pTVE226 | T3 | TNVsgRNa2 | cry9C | TNV (1) | T3 | T3 RNA Pol | T3-TNV-bar |
| pFM520 | pTFM520 | T3 | TNVsgRNA2 | cry9C | TNV (2) | T3 | T3 RNA Pol | T3-TNV-bar |

EXAMPLE 7

Plant Transformation and Analysis of Regenerated Plants

To obtain transformation of corn, the plasmids of the pFMseries of Example 5 (Table 15; preferably pFM414, pFM417, pFM514 and pFM517) and pVE236 are used for introduction in maize protoplasts [according to Wang et al. *Plant Cell Tissue and Organ Culture* 18: 33–46 (1989); Krens et al., *Nature* 296: 72–74 (1982)] for transient expression assays. Further they are used for electroporation of wounded type I callus (WO 92/09696) or they are introduced into corn protoplasts (EP 0469273) to obtain transgenic corn plants.

The plant transformation vectors of the pTFM series (preferably pTFM414, pTFM417, pTFM514 and pTFM517) are each mobilized into the *Agrobacterium tumefaciens* strain C58C1Rif$^R$ or LBA4011 carrying the avirulent Ti plasmid pGV2260 as described by Deblaere et al (1985). The respective Agrobacterium strains are used to transform oilseed rape using the method described by De Block et al (1989), while rice and corn are transformed according to WO 92109696. Transformed calli are selected on medium containing phosphinotricin, and resistant calli are regenerated into plants. For each transformation experiment, about 10 individual transformants are regenerated and analyzed by Southern blotting and PCR to verify gene integration patterns. Northern analysis and Reverse Transcription-PCR are employed to analyse mRNA levels. RNA from the chimeric cap-independently translated genes is found.

On the protein level, insect controlling amounts of Bt ICPs are found. Expression of the chimeric marker gene, translated in cap-independent manner is sufficient to allow selection of transformed plant cells on media containing phosphinotricin.

Plasmids pTVE228, pTVE229, pTVE230 and pTVE225 were introduced into *Agrobacterium tumefaciens* Ach5C3 containing the helper Ti-plasmid pGV4000 by mobilization. The resulting transconjugant strains A3684 (comprising pTVE228), A3685 (comprising pTVE229), A3686 (comprising pTVE230) and A3681(comprising pTVE225) were used for rice transformation according to WO 92/09696. The resulting transformed individual rice plants (110 from transformation with strain A3684; 22 from transformation with strain A3685; 101 from transformation with strain A3681, 91 from transformation with strain A3686) were either tested for the expression of proteins reactive in a Cry9C ELISA assay (for plants transformed by A3684, A3685 and A3681) or in a cry1Ab ELISA assay (for plants transformed by A3686). The cry1Ab ELISA assay was performed as described in U.S. Pat. No. 5,254,799.

Cry9C ELISA assay was performed using the following procedure:

Plant material was harvested, stored at −70° C. and crushed. To extract soluble proteins, 2 volumes of PBS (0.8 g/l NaCl; 0.02 g/l KCl; 0.115 g/l $Na_2HPO_4$; $KH_2PO_4$; pH7.3) were added to one volume of plant material, mixed and centrifuged for 15 minutes in the cold room. 50 pl of supernatant was applied per well in a microtiterplate (Costar "High binding" cat. Nr 3599) coated with immuno affinity purified rabbit antibodies against CRY9C. A sandwich ELISA was performed using purified goat antibodies against CRY 9C. Quantification was done using rabbit anti goat IgG peroxidase conjugate (SIGMA cat. Nr A-3450) and the TMB kit (Kirkegaard & Perry Laboratories cat. Nr. 50-65-00). A dilution series of purified CRY9C was reconstructed in each microtiterplate (120 to 0.94 ngCRY9C/ml untransformed plant protein extract). Untransformed plant protein extract was used as a blank.

It is clear from the results summarized in Table 16 that proteins reactive in a CRY9C ELISA assay can be found in transformed rice plants harboring cap-independently transcribed chimeric genes as described in the application. In addition, one plant transformed using A3686 contained proteins reactive in a CRY1Ab ELISA, estimated at a level of 20 ng CRY1Ab protein/ml plant protein extract. Moreover, as can be seen in the strain A3685 transformations (comprising pTVE229), a chimeric selectable gene comprising the bar coding region flanked by first and second translation enhancing sequences from TNV-A under control of a T7 promoter, allowed selection of transformed plants, based on PPT-resistance. Moreover, an ELISA assay to detect PAT protein, allowed estimation of PAT levels in leaves of the transformed rice plants between 40 to 270 ng PAT/ml plant protein extract (corresponding to 0.008 and 0.026% of total protein).

Plasmid pVE223 (Table 15) was used to transform corn protoplasts as described in EP 0469273. Leaves from 8 individual regenerated transgenic corn plants were assayed by CRY9C specific ELISA as described above. Samples from 3 plants clearly reacted positively, allowing estimation of levels CRY9C protein between 8–13 nglml plant protein extract.

TABLE 16

Results from the ELISA assay on transformed rice leaves

| | average amount of CRY9C in ng/ml protein extract | number of repeated experiments |
|---|---|---|
| | A3684 transformants | |
| A35-168B | 32 | 3 |
| A35-191B 3 | 6 | 2 |
| A35-205 | 22 | 3 |
| A35-216A | 9 | 2 |
| A35-216B | 10 | 2 |
| A35-216 | 15 | 2 |
| | A3685 transformants | |
| A35-224B 3 | 8 | 2 |
| | A3681 transformants | |
| A35-137B | 7 | 2 |
| A35-94 | 8 | 2 |
| A35-131A | 13 | 2 |
| A35-130B 3 | 10 | 2 |

TABLE 16-continued

Results from the ELISA assay on transformed rice leaves

| | average amount of CRY9C in ng/ml protein extract | number of repeated experiments |
|---|---|---|
| A35-131B | 12 | 1 |
| A35-104 | 14 | 2 |
| A35-118B 2 | 17 | 3 |

Leaves from two transgenic corn plants transformed by the CIG comprised on pVE223, which reacted positively in a CRY9C ELISA assay (N25-T49 and N25-T230) were tested in an insect assay, using as a negative control a transgenic corn plant comprising a P35S-bar chimeric gene (N23-T17). The leaves were each infested with 10 larvae (L1) of the European Corn Borer (*Ostrinia nubilalis*) and mortality as well as weight of the larvae were determined after 5 days. The results summarized in Table 17 indicate a growth inhibition and a mortality for larvae feeding on leaves of transgenic corn plants harboring the cap-independently expressed chimeric genes of the invention.

TABLE 17

Insect assay (*O. nubilalis*) on transgenic corn leaves.

| Transgenic corn plant | Mortality after 5 days (%) | Mean weight of the living larvae (mg) |
|---|---|---|
| N25-T49 | 40 | 0.18 |
| N25-T230 | 50 | 0.2 |
| N23-T17 | 0 | 1.0 |

All publications referred to in this application are hereby incorporated by reference.

We claim:

1. An isolated first translation enhancing sequence comprising a nucleotide sequence selected from: the nucleotide sequence at SEQ ID No. 1 from the nucleotide at position 2481 to the nucleotide at position 2619, the nucleotide sequence of SEQ ID No. 1 from the nucleotide at position 2461 to the nucleotide at position 2612, the nucleotide sequence of SEQ ID No. 1 from the nucleotide at position 2461 to the nucleotide at position 2803, and the nucleotide sequence of SEQ ID No. 1 from the nucleotide at position 2461 to the nucleotide at position 2598.

2. An isolated second translation enhancing sequence comprising a nucleotide sequence selected from: the nucleotides sequence of SEQ ID No. 1 from the nucleotide at position 3399 to the nucleotide at position 3684, the nucleotide sequence of SEQ ID No. 1 from the nucleotide at position 3429 to the nucleotide at position 3611 and the nucleotide sequence of SEQ ID NQ. 1 from the nucleotide at position 3472 to the nucleotide at position 3611.

3. An isolated DNA that is a first translation enhancing sequence of claim 1.

4. An isolated DNA that is a second translation enhancing sequence of claim 2.

5. A DNA molecule comprising:

i.) an isolated DNA encoding a first translation enhancing sequence comprising a nucleotide sequence selected from: the nucleotides sequence of SEQ ID No. 1 from the nucleotide at position 2461 to the nucleotide at position 2619, the nucleotide sequence of SEQ ID No. 1 from the nucleotide at position 2461 to the nucleotide at position 2612, the nucleotide sequence of SEQ ID No. 1 from the nucleotide at position 2461 to the nucleotide at position 2603, and the nucleotide sequence of SEQ ID No. 1 from the nucleotide at position 2481 to the nucleotide at position 2958; and ii) an isolated DNA encoding a second translation enhancing sequence comprising a nucleotide sequence selected from: the nucleotide sequence of SEQ ID No. 1 from the nucleotide at position 3399 to the nucleotide at position 3684, the nucleotide sequence of SEQ ID No. 1 from the nucleotide at position 3429 to the nucleotide at position 3611 and the nucleotide sequence of SEQ ID No. 1 from the nucleotide at position 3472 to the nucleotide at position 3611 wherein said isolated DNA encoding a first translation enhancing sequence and said isolated DNA encoding a second translation enhancing sequence are operably linked to a heterologous DNA fragment encoding a protein or polypeptide of interest.

* * * * *

SEQUENCE LISTING

```
<160> NUMBER OF SEQ ID NOS: 41

<210> SEQ ID NO 1
<211> LENGTH: 3684
<212> TYPE: DNA
<213> ORGANISM: Tobacco necrosis virus

<400> SEQUENCE: 1

agtattcata ccaagaatac caaataggtg caaggcctta ctcagctaaa gagtctaaaa     60

tggagctacc aaaccaacac aagcaaacgg ccgccgaggg tttcgtatct ttcctaaact    120

ggctatgcaa cccatggaga cgacagcgaa cagtcaacgc tgcagttgcg ttccaaaaag    180

atcttctcgc cattgaggat tccgagcatt tggatgacat caatgagtgt ttcgaggagt    240

ctgctggggc acaatctcag cgaactaagg ttgtcgccga cggagcatat gcccccgcaa    300

aatccaacag gacccgccga gttcgtaagc agaagaagca caagtttgta aaatatcttg    360

tcaacgaagc tcgtgccgag tttggattgc ccaaaccaac tgaggcaaac agacttatgg    420

tccaacattt cttgctcaga gtgtgcaagg attggggcgt tgttactgcc cacgtacacg    480

gcaatgttgc actagctttg ccactggtgt tcatcccaac ggaagatgat ctgctatcac    540

gagcattgat gaacacacat gctactagag ccgctgtacg aggcatggac aatgtccaag    600
```

-continued gggaggggtg gtggaacaat aggttgggga ttgggggcca ggtcggactg gccttccggt 660
ccaaataggg gtgccttgaa aggaggccag gattctccac gtccgtttcg cgtggggaac 720
atcctgatct ggtggtcata ccatcagggc gccctgagaa acagcgtcag ttgttacgct 780
atagtggtat aggcggccat ttattaatcg gcatccacaa caactctctt tccaacctgc 840
gtaggggctt gatggaaaga gtattctatg tcgaggggcc caatgggctt caagacgccc 900
ctaagcccgt caagggagct tttcgaaccc ttgataagtt tcgtgatctc tatactaaaa 960
atagttggcg tcatacccct gtaactagtg aacaattcct aatgaattac acgggcagga 1020
aactgactat ttacagagag gcggttgata gtttgtcgca tcaacccctt agctcacgag 1080
atgcgaaact aaagacattc gtgaaggccg aaaaattaaa tctttctaag aagcctgacc 1140
ctgctcccag ggtcatccaa cctagatcgc ctcggtataa cgtttgtttg ggcaggtacc 1200
tccgacatta tgagcatcac gcgtttaaaa ccattgccaa gtgctttggg gaaatcacgg 1260
tcttcaaagg gtttactctg gagcaacaag ggaaatcat gcgctcgaag tggaataaat 1320
atgttaatcc cgtcgcagtc ggactcgacg ccagtcgttt cgaccaacac gtgtctgttg 1380
aagcactcga gtatgagcat gaattttacc tcagagacta cccaaatgat aaacagctaa 1440
aatggctgct aaagcagcaa ttgtgcaacg taggaacggc attcgccagt gacggcatta 1500
taaaatacaa gaagaagggt tgtagaatga gcggagacat gaacacgagt ttgggcaact 1560
gcattctaat gtgcgccatg gtctacgggt tgaaagaaca cttaaacatc aatttgtccc 1620
ttgcaaataa tggggatgac tgcgtcattg tctgtgagaa agcggattta aagaaattga 1680
caagcagcat cgagccatat ttcaagcagt ttggattcaa gatggaagtg gaaaaacccg 1740
tggatatatt tgagcgcata gaattttgcc aaacccaacc tgtgttcgat ggatcccagt 1800
acatcatggt acgcaaacct tctgtggtaa catctaaaga cgtcactagc cttatcccat 1860
gtcaaacgaa agcacaatac gcagaatggc tgcaagctgt aggtgagtgt ggcatgagca 1920
ttaacggtgg gattcctgtc atgcagaatt tctaccaaaa gctccaaact ggcatccgcc 1980
gcacaaaatt caccaagacc ggcgagttcc agacgaacgg attggggtat cactctagat 2040
atatgcatag agtggcccgg gttccttcgc ctgaaacccg tttatccttc tatctagctt 2100
tcggtatcac accagacctc caagaagcat tggagatctt ctatgatacc cacaggcttg 2160
agttggatga tgttatccca actgatacct accaagtgtc aggagagcat ttgatcaatg 2220
gattaccaaa ctgatgtaac ggaggacaat gtgcaaatac gcggtcgggc taggagcgtt 2280
gagggtaaga aacacaatgg ttcgggatta actggcgtta agcgtcacgc ggtgagcgaa 2340
acatctcaga aatcacagca aggtactggc aatggaacta tgaccaatat agccgaagaa 2400
cagaccatta ccgtgacata caactttaac ttttaagtta tggctgcgtg tcgctgttgt 2460
gatacttcac caggtattac actattccct tactttgcaa ttctcatcct tatattggca 2520
atacttgttg tagggactcc caatcaacaa tatcaccatt ctccaagcac ttacgagtac 2580
aagactcaac acatttcgat cgcaaaatag acatggcagg aaagaagaac aacaacaacg 2640
gtcagtatat aatactgcgt actccagagc aacaggtgga gatagaccag cgcaacgccc 2700
gtcgtgctca aatgggtcgc atgaagaagg ctagacagcc cgttcagcga tacttacagc 2760
aacacgggtt gcgaaacgga ttgtccggta gagggggcta catagtggct cccacctccg 2820
ggggggttgt cactcgaccc atagtgccga aattctccaa caggggagat tccactatag 2880
tccgtaacac tgagattttg aacaaccaaa tcttagcggc gctaggcgca ttcaatacaa 2940
caaactccgc actgattgca gcagcaccat catggctggc tagcatcgct gatctttaca 3000
gtaaatacag atggctctca tgtgagatca tctacattcc aaaatgcccc accaccacca 3060
gtggatcaat tgccatggct ttcacatacg acagaaatga cgctgcaccc accgcaaggg 3120
ctcagctgtc acaatcttac aaggccatca attttccacc gtatgcggga tacgacggag 3180
cagcatattt gaattcgaac cagggagctg ggtcagccat cgccgttcaa cttgatgtta 3240
ccaagttgga caagccatgg taccccacta tctcctctgc cggcttcggg gcgctcagcg 3300
tcctcgatca gaaccaattc tgccccgcgt cccttgtggt cgctagcgat gggggacccg 3360
ctactgctac tccagcaggg gaccttttca tcaagtacgt gattgagttc attgaaccaa 3420
tcaacccaac aatgaacgtc tagttctttg tactgtaact tggctaatgc ctaaggtgga 3480
gtcacaccat tggagacgga gacggatcct gggaaacagg cttgacgggc ggggggtggt 3540
gcccccgacg acgcatcact ccggatacca atggtacacc actatggcag ggtctgccaa 3600
ggtcttgtgc accaagaacc cctggaaacg ggggggaggg gggtagcaca tatcatccag 3660
attgaggggc ctttgcccca cccc 3684

<210> SEQ ID NO 2
<211> LENGTH: 1245
<212> TYPE: DNA
<213> ORGANISM: Satellite tobacco necrosis virus

<400> SEQUENCE: 2
agtaaagaca ggaaacttta ccgactatca gaatgacaaa acgtcaaagc aaacaatcaa 60
accgcaagag cgttgcatca caggtgcgta gtattgttga gtcaatggct gagcagaagc 120
gatttgcttt tcttacgaac accaacacag tcactacagc aggtaccgtg atcaacctga 180
gcaacaacat cgtgcaagga gatgaccttg ttaatcgcac cggagaccag attaagacca 240
tacaccagac tttattgact cggtgtacag gaattaccaa cagccaaagc tttcggttca 300
tctggtttcg tgacaacacc aataggggga ctacaccggc tgtgactgag gtgttagaca 360
gtgctagtat aacatcccag tataacccca ctacgttcca gcaaaagagg ttcactgttt 420
tccaagattt catgttggat acctctatag ttggacgtgt gattgtccat cggactgccg 480
ttgataagaa acggcgtgcg atattttaca acggtgctgc ttctgtagcc gcgtcaaatg 540
gccccggtgc cacatttgta cttgtcattg gatcacatgc cactggacag tatgatgtga 600
cagccgagat tgtttatctg gacatgtaga ccatggtcat gatgatgata gtgaaggacg 660
ctgaaagatg cgtagctacc ctcctggtgc acttcctggt gcaaagcaga accaaagggt 720
acggtggtac ggcggacagt agtcctgaac tagtaaatca ggaccgggag aaaaccagct 780
gacggctaaa tccattccca ctagtgtatt agtggaacga ggccccgcgt gaattggggt 840
ggctgcatgg ggtggaaaac catgtggtcg cagtcatttc tcctatgcat tattgtctca 900
atacttgtgt gcaacaatgc tgttaatcaa cgtagcactc aacatcactt caaaaccccc 960
tccatgtcac aagaatcaag atgcatgtct gtgtttagcg gtatatattt tgcatccact 1020
tgatcgtgat tttgccctgg gcacctcgcg cggttggtac ccgcggagac tccccacagc 1080
aacatggcat taggcaggga taaggtatag tgactagaca aatgcgcgtg aagctggaaa 1140
gtccggttag cagtggggtt gtgcggaatg cagcctcaac aaggtatagc tgctgcatag 1200
gagatgtgaa cctttcaaac ttgaattcaa gtctcatgac tgccc 1245

<210> SEQ ID NO 3
<211> LENGTH: 781
<212> TYPE: DNA
<213> ORGANISM: Artificial Sequence
<220> FEATURE:

<223> OTHER INFORMATION: coding region = nt 5 through 664
<220> FEATURE:
<223> OTHER INFORMATION: Description of Artificial
Sequence:chloramphenicol acetyltransferase gene

<400> SEQUENCE: 3

```
atcgatggag aaaaaaatca ctggatatac caccgttgat atatcccaat ggcatcgtaa     60

agaacatttt gaggcatttc agtcagttgc tcaatgtacc tataaccaga ccgttcagct    120

ggatattacg gcctttttaa agaccgtaaa gaaaaataag cacaagtttt atccggcctt    180

tattcacatt cttgcccgcc tgatgaatgc tcatccggaa ttccgtatgg caatgaaaga    240

cggtgagctg gtgatatggg atagtgttca cccttgttac accgttttcc atgagcaaac    300

tgaaacgttt tcatcgctct ggagtgaata ccacgacgat ttccggcagt ttctacacat    360

atattcgcaa gatgtggcgt gttacggtga aaacctggcc tatttcccta aagggtttat    420

tgagaatatg tttttcgtct cagccaatcc ctgggtgagt ttcaccagtt ttgatttaaa    480

cgtggccaat atggacaact tcttcgcccc cgttttcacc atgggcaaat attatacgca    540

aggcgacaag gtgctgatgc cgctggcgat tcaggttcat catgccgtct gtgatggctt    600

ccatgtcggc agaatgctta atgaattaca acagtactgc gatgagtggc agggcggggc    660

gtaatttttt taaggcagtt attggtgccc ttaaacgcct ggttgctacg cctgaataag    720

tgataataag cggatgaatg gcagaaattc gaaagcaaat tcgacccatc gcgcgtctag    780

a                                                                    781
```

<210> SEQ ID NO 4
<211> LENGTH: 790
<212> TYPE: DNA
<213> ORGANISM: Artificial Sequence
<220> FEATURE:
<223> OTHER INFORMATION: Description of Artificial Sequence:inserted DNA
fragment in pXD324

<400> SEQUENCE: 4

```
ggatccgtat ttttacaaca attaccacaa caaaacaaac aacaaacaac attacaattt     60

actattctag aattaccatg ggcccagaac gacgcccggc cgacatccgc cgtgccaccg    120

aggcggacat gccggcggtc tgcaccatcg tcaaccacta catcgagaca agcacggtca    180

acttccgtac cgagccgcag gaaccgcagg agtggacgga cgacctcgtc cgtctgcggg    240

agcgctatcc ctggctcgtc gccgaggtgg acggcgaggt cgccggcatc gcctacgcgg    300

gcccctggaa ggcacgcaac gcctacgact ggacggccga gtcgaccgtg tacgtctccc    360

cccgccacca gcggacggga ctgggctcca cgctctacac ccacctgctg aagtccctgg    420

aggcacaggg cttcaagagc gtggtcgctg tcatcgggct gcccaacgac ccgagcgtgc    480

gcatgcacga ggcgctcgga tatgcccccc gcggcatgct gcgggcggcc ggcttcaagc    540

acgggaactg gcatgacgtg ggtttctggc agctggactt cagcctgccg gtaccgcccc    600

gtccggtcct gcccgtcacc gagatctgat ctcacgcgaa ttccggggat cctctagagt    660

cgacctgcag gcatgcaagc taaaaaaaaa aaaaaaaaaa aaaaaaaaaa aaaagaaaaa    720

aaaaaaaaaa aaaaaaaaaa aaaaaaagaa aaaaaaaaaa aaaaaaaaaa aaaaaaaaaa    780

gcttgtattc                                                           790
```

<210> SEQ ID NO 5
<211> LENGTH: 1897
<212> TYPE: DNA
<213> ORGANISM: Artificial Sequence
<220> FEATURE:

<223> OTHER INFORMATION: coding region = nt 13 through 1890
<220> FEATURE:
<223> OTHER INFORMATION: Description of Artificial Sequence:native
      coding sequence of cry9C(truncated)

<400> SEQUENCE: 5

```
ggtaccaaaa ccatggctga ttacttacaa atgacagatg aggactacac tgattcttat     60

ataaatccta gtttatctat tagtggtaga gatgcagttc agactgcgct tactgttgtt    120

gggagaatac tcggggcttt aggtgttccg ttttctggac aaatagtgag tttttatcaa    180

ttccttttaa atacactgtg gccagttaat gatacagcta tatgggaagc tttcatgcga    240

caggtggagg aacttgtcaa tcaacaaata acagaatttg caagaaatca ggcacttgca    300

agattgcaag gattaggaga ctcttttaat gtatatcaac gttcccttca aaattggttg    360

gctgatcgaa atgatacacg aaatttaagt gttgttcgtg ctcaatttat agctttagac    420

cttgattttg ttaatgctat tccattgttt gcagtaaatg gacagcaggt tccattactg    480

tcagtatatg cacaagctgt gaatttacat ttgttattat taaaagatgc atctcttttt    540

ggagaaggat ggggattcac acaggggggaa atttccacat attatgaccg tcaattggaa    600

ctaaccgcta agtacactaa ttactgtgaa acttggtata atacaggttt agatcgttta    660

agaggaacaa atactgaaag ttggttaaga tatcatcaat tccgtagaga aatgacttta    720

gtggtattag atgttgtggc gctatttcca tattatgatg tacgacttta tccaacggga    780

tcaaacccac agcttacacg tgaggtatat acagatccga ttgtatttaa tccaccagct    840

aatgttggac tttgccgacg ttggggtact aatccctata atactttttc tgagctcgaa    900

aatgccttca ttcgcccacc acatcttttt gataggctga atagcttaac aatcagcagt    960

aatcgatttc cagtttcatc taattttatg gattattggt caggacatac gttacgccgt   1020

agttatctga acgattcagc agtacaagaa gatagttatg gcctaattac aaccacaaga   1080

gcaacaatta atcccggagt tgatggaaca aaccgcatag agtcaacggc agtagatttt   1140

cgttctgcat tgataggtat atatggcgtg aatagagctt cttttgtccc aggaggcttg   1200

tttaatggta cgacttctcc tgctaatgga ggatgtagag atctctatga tacaaatgat   1260

gaattaccac cagatgaaag taccggaagt tcaacccata gactatctca tgttaccttt   1320

tttagctttc aaactaatca ggctggatct atagctaatg caggaagtgt acctacttat   1380

gtttggaccc gtcgtgatgt ggaccttaat aatacgatta ccccaaatag aattacacaa   1440

ttaccattgg taaaggcatc tgcacctgtt tcgggtacta cggtcttaaa aggtccagga   1500

tttacaggag gggtatact ccgaagaaca actaatggca catttggaac gttaagagta   1560

acggttaatt caccattaac acaacaatat cgcctaagag ttcgttttgc ctcaacagga   1620

aatttcagta taagggtact ccgtggaggg gtttctatcg gtgatgttag attagggagc   1680

acaatgaaca gagggcagga actaacttac gaatcctttt tcacaagaga gtttactact   1740

actggtccgt tcaatccgcc ttttacattt acacaagctc aagagattct aacagtgaat   1800

gcagaaggtg ttagcaccgg tggtgaatat tatatagata gaattgaaat tgtccctgtg   1860

aatccggcac gagaagcgga agaggactga ggctagc                            1897
```

<210> SEQ ID NO 6
<211> LENGTH: 1788
<212> TYPE: DNA
<213> ORGANISM: Artificial Sequence
<220> FEATURE:
<223> OTHER INFORMATION: coding region = nt 9 through 1781
<220> FEATURE:
<223> OTHER INFORMATION: Description of Artificial Sequence:native coding sequence of cry1A(b)(truncated)

<400> SEQUENCE: 6

```
ccaaaaccat ggctatagaa actggttaca ccccaatcga tatttccttg tcgctaacgc     60
aatttctttt gagtgaattt gttcccggtg ctggatttgt gttaggacta gttgatataa    120
tatggggaat ttttggtccc tctcaatggg acgcatttct tgtacaaatt gaacagttaa    180
ttaaccaaag aatagaagaa ttcgctagga accaagccat ttctagatta gaaggactaa    240
gcaatcttta tcaaatttac gcagaatctt ttagagagtg ggaagcagat cctactaatc    300
cagcattaag agaagagatg cgtattcaat tcaatgacat gaacagtgcc cttacaaccg    360
ctattcctct tttgcagtt caaaattatc aagttcctct tttatcagta tatgttcaag    420
ctgcaaattt acatttatca gttttgagag atgtttcagt gtttggacaa aggtggggat    480
ttgatgccgc gactatcaat agtcgttata atgatttaac taggcttatt ggcaactata    540
cagatcatgc tgtacgctgg tacaatacgg gattagagcg tgtatgggga ccggattcta    600
gagattggat aagatataat caatttagaa gagaattaac actaactgta ttagatatcg    660
tttctctatt tccgaactat gatagtagaa cgtatccaat tcgaacagtt tcccaattaa    720
caagagaaat ttatacaaac ccagtattag aaaattttga tggtagtttt cgaggctcgg    780
ctcagggcat agaaggaagt attaggagtc cacatttgat ggatatactt aacagtataa    840
ccatctatac ggatgctcat agaggagaat attattggtc agggcatcaa ataatggctt    900
ctcctgtagg gttttcgggg ccagaattca cttttccgct atatggaact atgggaaatg    960
cagctccaca acaacgtatt gttgctcaac taggtcaggg cgtgtataga acattatcgt   1020
ccactttata tagaagacct tttaatatag ggataaataa tcaacaacta tctgttcttg   1080
acgggacaga atttgcttat ggaacctcct caaatttgcc atccgctgta tacagaaaaa   1140
gcggaacggt agattcgctg gatgaaatac cgccacagaa taacaacgtg ccacctaggc   1200
aaggatttag tcatcgatta agccatgttt caatgtttcg ttcaggcttt agtaatagta   1260
gtgtaagtat aataagagct cctatgttct cttggataca tcgtagtgct gaatttaata   1320
atataattcc ttcatcacaa attacacaaa tacctttaac aaaatctact aatcttggct   1380
ctggaacttc tgtcgttaaa ggaccaggat ttacaggagg agatattctt cgaagaactt   1440
cacctggcca gatttcaacc ttaagagtaa atattactgc accattatca caaagatatc   1500
gggtaagaat tcgctacgct tctaccacaa atttacaatt ccatacatca attgacggaa   1560
gacctattaa tcaggggaat ttttcagcaa ctatgagtag tgggagtaat ttacagtccg   1620
gaagctttag gactgtaggt tttactactc cgtttaactt ttcaaatgga tcaagtgtat   1680
ttacgttaag tgctcatgtc ttcaattcag gcaatgaagt ttatatagat cgaattgaat   1740
ttgttccggc agaagtaacc tttgaggcag aatatgattg aggctagc                1788
```

<210> SEQ ID NO 7
<211> LENGTH: 42
<212> TYPE: DNA
<213> ORGANISM: Artificial Sequence
<220> FEATURE:
<223> OTHER INFORMATION: Description of Artificial Sequence:synthesized primer

<400> SEQUENCE: 7

```
tagctcaggg atccggtctc gatacttcac caggtattac ac                          42
```

<210> SEQ ID NO 8
<211> LENGTH: 19

-continued

<212> TYPE: DNA
<213> ORGANISM: Artificial Sequence
<220> FEATURE:
<223> OTHER INFORMATION: Description of Artificial Sequence:synthesized primer

<400> SEQUENCE: 8
gctgctgcaa tcagtgcgg 19

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence:synthesized primer

<400> SEQUENCE: 9
gtactgtaac ttggctaatg cc 22

<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence:synthesized primer

<400> SEQUENCE: 10
atgtagactg caggtctccg gggtggggca aaggcc 36

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:synthesized primer

<400> SEQUENCE: 11
tcccatatca ccagctcacc 20

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence:synthesized primer

<400> SEQUENCE: 12
cttcgccccc gttttcacca tgggc 25

<210> SEQ ID NO 13
<211> LENGTH: 41
<212> TYPE: DNA
<213> ORGANISM: Artificial Sequence
<220> FEATURE:
<223> OTHER INFORMATION: Description of Artificial Sequence:synthesized primer

<400> SEQUENCE: 13
ctcaatcaca ccaataactg ccttagctag cttacgcccc g 41

<210> SEQ ID NO 14
<211> LENGTH: 40
<212> TYPE: DNA
<213> ORGANISM: Artificial Sequence
<220> FEATURE:
<223> OTHER INFORMATION: Description of Artificial Sequence:synthesized primer

<400> SEQUENCE: 14
gcgatgagtc gcagggcggg gcgtaagcta gctaaggcag 40

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence:synthesized primer

<400> SEQUENCE: 15
gcctgtttcc caggatccgt ctccg 25

<210> SEQ ID NO 16
<211> LENGTH: 38
<212> TYPE: DNA
<213> ORGANISM: Artificial Sequence
<220> FEATURE:
<223> OTHER INFORMATION: Description of Artificial Sequence:synthesized primer

<400> SEQUENCE: 16
gattgagttc attgaaccaa tcgctagcac aatgaacg 38

<210> SEQ ID NO 17
<211> LENGTH: 40
<212> TYPE: DNA
<213> ORGANISM: Artificial Sequence
<220> FEATURE:
<223> OTHER INFORMATION: Description of Artificial Sequence:synthesized primer

<400> SEQUENCE: 17
gtacaaagaa ctagacgttc attgtgctag cgattggttc 40

<210> SEQ ID NO 18
<211> LENGTH: 45
<212> TYPE: DNA
<213> ORGANISM: Artificial Sequence
<220> FEATURE:
<223> OTHER INFORMATION: Description of Artificial Sequence:synthesized primer

<400> SEQUENCE: 18
cggccagcat atgttattaa ccctcactaa agatacttca ccagg 45

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence:synthesized primer

<400> SEQUENCE: 19
aagaagttgt ccatattggc ca 22

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence:synthesized primer

<400> SEQUENCE: 20
acggtcacag cttgtctgta ag                                              22

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence:synthesized
      primer

<400> SEQUENCE: 21
ctttaccgac tatcagaatg acacgcgtaa tac                                  33

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence:synthesized
      primer

<400> SEQUENCE: 22
taaagacagg aaactttact gactaccatg                                      30

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence:synthesized
      primer

<400> SEQUENCE: 23
catggtagtc agtaaagttt cctgtcttta                                      30

<210> SEQ ID NO 24
<211> LENGTH: 139
<212> TYPE: DNA
<213> ORGANISM: Artificial Sequence
<220> FEATURE:
<221> NAME/KEY: stem_loop
<222> LOCATION: (67)..(106)
<223> OTHER INFORMATION: standard_name = "hairpin from T3 RNA polymerase
      terminator"
<220> FEATURE:
<223> OTHER INFORMATION: Description of Artificial Sequence:T3 RNA
      polymerase terminator

<400> SEQUENCE: 24
ctgcagcgga ccgactagtc caccctgaaa gctcgttgtg attgggataa caatctacta     60
atatgcaaac cccttgggtt ccctctttgg gagtctgagg ggttttttgc tttaaccctc    120
tagagctcgg ccgaagctt                                                 139

<210> SEQ ID NO 25
<211> LENGTH: 43
<212> TYPE: DNA
<213> ORGANISM: Artificial Sequence
<220> FEATURE:
<223> OTHER INFORMATION: Description of Artificial Sequence:synthesized
      primer

<400> SEQUENCE: 25
gtattaccat ggtcatcacg tgtcattctg atagtcggta aag                       43

-continued

<210> SEQ ID NO 26
<211> LENGTH: 45
<212> TYPE: DNA
<213> ORGANISM: Artificial Sequence
<220> FEATURE:
<223> OTHER INFORMATION: Description of Artificial Sequence:synthesized
primer

<400> SEQUENCE: 26
gtaccggttc gaagcttgat atcggccgca tgctgcagct agccc 45

<210> SEQ ID NO 27
<211> LENGTH: 49
<212> TYPE: DNA
<213> ORGANISM: Artificial Sequence
<220> FEATURE:
<223> OTHER INFORMATION: Description of Artificial Sequence:synthesized
primer

<400> SEQUENCE: 27
catggggcta gctgcagcat gcggccgata tcaagcttcg aaccggtac 49

<210> SEQ ID NO 28
<211> LENGTH: 34
<212> TYPE: DNA
<213> ORGANISM: Artificial Sequence
<220> FEATURE:
<223> OTHER INFORMATION: Description of Artificial Sequence:synthesized
primer

<400> SEQUENCE: 28
ctatgtacca tgggtgtcat tctgatagtc ggta 34

<210> SEQ ID NO 29
<211> LENGTH: 73
<212> TYPE: DNA
<213> ORGANISM: Artificial Sequence
<220> FEATURE:
<223> OTHER INFORMATION: Description of Artificial Sequence:synthesized
primer

<400> SEQUENCE: 29
gtaccttagg ttcgaagcta gcggtccgtt aaccatggtt ttggcgatcg aaatgtgttg 60
agtcttgtac tcg 73

<210> SEQ ID NO 30
<211> LENGTH: 39
<212> TYPE: DNA
<213> ORGANISM: Artificial Sequence
<220> FEATURE:
<223> OTHER INFORMATION: Description of Artificial Sequence:synthesized
primer

<400> SEQUENCE: 30
cggccagcat atgcgcgcct gtaatacgac tcactatag 39

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence:synthesized
primer

<400> SEQUENCE: 31
agttcctcca cctgtcgc 18

<210> SEQ ID NO 32
<211> LENGTH: 40
<212> TYPE: DNA
<213> ORGANISM: Artificial Sequence
<220> FEATURE:
<223> OTHER INFORMATION: Description of Artificial Sequence:synthesized
primer

<400> SEQUENCE: 32
cggccagcat atgcgcgcct gttattaacc ctcactaaag 40

<210> SEQ ID NO 33
<211> LENGTH: 28
<212> TYPE: DNA
<213> ORGANISM: Artificial Sequence
<220> FEATURE:
<223> OTHER INFORMATION: Description of Artificial Sequence:synthesized
primer

<400> SEQUENCE: 33
gccaagttac acgtacaaag aactagac 28

<210> SEQ ID NO 34
<211> LENGTH: 1893
<212> TYPE: DNA
<213> ORGANISM: Artificial Sequence
<220> FEATURE:
<223> OTHER INFORMATION: coding region = nt 9 through 1886
<220> FEATURE:
<223> OTHER INFORMATION: Description of Artificial Sequence:synthetic
fragment encoding CRY9C (truncated)

<400> SEQUENCE: 34
ccaaaaccat ggctgactac ctgcagatga ccgacgagga ctacaccgac agctacatca 60
accccagcct gagcatcagc ggtcgcgacg ccgtgcagac cgctctgacc gtggtgggtc 120
gcatcctggg tgccctgggc gtgcccttca gcggtcagat cgtgagcttc taccagttcc 180
tgctgaacac cctgtggcca gtgaacgaca ccgccatctg ggaagctttc atgcgccagg 240
tggaggagct ggtgaaccag cagatcaccg agttcgctcg caaccaggcc ctggctcgcc 300
tgcagggcct gggcgacagc ttcaacgtgt accagcgcag cctgcagaac tggctggccg 360
accgcaacga cacccgcaac ctgagcgtgg tgagggccca gttcatcgcc ctggacctgg 420
acttcgtgaa cgccatcccc ctgttcgccg tgaacggcca gcaggtgccc ctgctgagcg 480
tgtacgccca ggccgtgaac ctgcacctgc tgctgctgaa ggatgcatcc ctgttcggcg 540
agggctgggg cttcacccag ggcgagatca gcacctacta cgaccgccag ctcgagctga 600
ccgccaagta caccaactac tgcgagacct ggtacaacac cggtctggac cgcctgaggg 660
gcaccaacac cgagagctgg ctgcgctacc accagttccg cagggagatg accctggtgg 720
tgctggacgt ggtggccctg ttcccctact acgacgtgcg cctgtacccc accggcagca 780
acccccagct gacacgtgag gtgtacaccg accccatcgt gttcaaccca ccagccaacg 840
tgggcctgtg ccgcaggtgg ggcaccaacc cctacaacac cttcagcgag ctggagaacg 900
ccttcatcag gccaccccac ctgttcgacc gcctgaacag cctgaccatc agcagcaatc 960
gattccccgt gagcagcaac ttcatggact actggagcgg tcacaccctg cgcaggagct 1020
acctgaacga cagcgccgtg caggaggaca gctacggcct gatcaccacc accagggcca 1080
ccatcaaccc aggcgtggac ggcaccaacc gcatcgagag caccgctgtg gacttccgca 1140
gcgctctgat cggcatctac ggcgtgaaca gggccagctt cgtgccaggt ggcctgttca 1200
acggcaccac cagcccagcc aacggtggct gccgagatct gtacgacacc aacgacgagc 1260
tgccacccga cgagagcacc ggcagcagca cccaccgcct gagccacgtc accttcttca 1320
gcttccagac caaccaggct ggcagcatcg ccaacgctgg cagcgtgccc acctacgtgt 1380
ggaccaggag ggacgtggac ctgaacaaca ccatcacccc caaccgcatc acccagctgc 1440
ccctggtgaa ggccagcgct cccgtgagcg gcaccaccgt gctgaagggt ccaggcttca 1500
ccggtggcgg tatactgcgc aggaccacca acggcacctt cggcaccctg cgcgtgaccg 1560
tgaattcccc actgacccag cagtaccgcc tgcgcgtgcg cttcgccagc accggcaact 1620
tcagcatccg cgtgctgagg ggtggcgtga gcatcggcga cgtgcgcctg ggcagcacca 1680
tgaacagggg ccaggagctg acctacgaga gcttcttcac ccgcgagttc accaccaccg 1740
gtcccttcaa cccacccttc accttcaccc aggcccagga gatcctgacc gtgaacgccg 1800
agggcgtgag caccggtggc gagtactaca tcgaccgcat cgagatcgtg cccgtgaacc 1860
cagctcgcga ggccgaggag gactgaggct agc 1893

<210> SEQ ID NO 35
<211> LENGTH: 1034
<212> TYPE: DNA
<213> ORGANISM: Artificial Sequence
<220> FEATURE:
<221> NAME/KEY: 3'UTR
<222> LOCATION: Complement((27)..(249))
<223> OTHER INFORMATION: function = “3' end formation signal of CaMV”
<220> FEATURE:
<223> OTHER INFORMATION: coding region = nt 262 through 363 (complement)
<220> FEATURE:
<221> NAME/KEY: 5'UTR
<222> LOCATION: Complement((370)..(429))
<223> OTHER INFORMATION: standard_name = “leader from cab22L gene from Petunia”
<220> FEATURE:
<221> NAME/KEY: promoter
<222> LOCATION: Complement((434)..(960))
<223> OTHER INFORMATION: standard_name = “CaMV35S promoter”
<220> FEATURE:
<223> OTHER INFORMATION: Description of Artificial Sequence:inserted fragment of pFM409

<400> SEQUENCE: 35
cctgcaggca attggtacca tgcatgatct ggattttagt actggatttt ggttttagga 60
attagaaatt ttattgatag aagtatttta caaatacaaa tacatactaa gggtttctta 120
tatgctcaac acatgagcga aaccctatag gaaccctaat tcccttatct gggaactact 180
cacacattat tatggagaaa atagagagag atagatttgt agagagagac tggtgatttc 240
agcgtgtcca agcttgctag ctagtcctaa cacaaatcca gcaccgggaa caaattcact 300
caaaagaaat tgcgttagcg acaaggaaat atcgattggg gtgtaaccgg tctcgatagc 360
catggttttg gtttaataag aagagaaaag agttcttttg ttatggctga agtaatagag 420
aaatgagctc gagtcctctc caaatgaaat gaacttcctt atatagagga agggtcttgc 480
gaaggatagt gggattgtgc gtcatccctt acgtcagtgg agatatcaca tcaatccact 540
tgctttgaag acgtggttgg aacgtcttct ttttccacga tgctcctcgt gggtgggggt 600
ccatctttgg gaccactgtc ggcagaggca tcttgaacga tagcctttcc tttatcgcaa 660
tgatggcatt tgtaggtgcc accttccttt tctactgtcc ttttgatgaa gtgacagata 720
gctgggcaat ggaatccgag gaggtttccc gatattaccc tttgttgaaa agtctcaata 780
gccctttggt cttctgagac tgtatctttg atattcttgg agtagacgag agtgtcgtgc 840
tccaccatgt tgacgaagat ttcttcttg tcattgagtc gtaaaagact ctgtatgaac 900
tgttcgccag tcttcacggc gagttctgtt agatcctcga tctgaatttt tgactccatg 960
tatggtgcat ggcgcgccat atgcccgggc cctgtacagc ggccgcgtta acgcgtatac 1020
tctagagcga tcgc 1034

<210> SEQ ID NO 36
<211> LENGTH: 35
<212> TYPE: DNA
<213> ORGANISM: Artificial Sequence
<220> FEATURE:
<223> OTHER INFORMATION: Description of Artificial Sequence:nucleotide sequence preceding the T7 RNA polymerase in pFM410

<400> SEQUENCE: 36
ccaaaaccat ggctcccaag aagaagcgca aggtt 35

<210> SEQ ID NO 37
<211> LENGTH: 105
<212> TYPE: DNA
<213> ORGANISM: Artificial Sequence
<220> FEATURE:
<223> OTHER INFORMATION: Location 1..25; label = RB; note = Right Border sequence from the T-DNA of pTFM600"
<220> FEATURE:
<223> OTHER INFORMATION: Location 26..80; label = MCS; note = "multiple cloning site"
<220> FEATURE:
<223> OTHER INFORMATION: Location 81..105; label = LB; note = "Left Border sequence from the T-DNA of pTFM600"
<220> FEATURE:
<223> OTHER INFORMATION: Description of Artificial Sequence:pTFM600 T-DNA

<400> SEQUENCE: 37
aattacaacg gtatatatcc tgccagtact cggccgtcga cctgcaggaa ttctagatac 60
gtagcgatcg ccatggagcc atttacaatt gaatatatcc tgccg 105

<210> SEQ ID NO 38
<211> LENGTH: 1003
<212> TYPE: DNA
<213> ORGANISM: Artificial Sequence
<220> FEATURE:
<221> NAME/KEY: 5'UTR
<222> LOCATION: (18)..(49)
<223> OTHER INFORMATION: standard_name = "STNV-2 leader"
<220> FEATURE:
<223> OTHER INFORMATION: coding region = nt 50 through 985
<220> FEATURE:
<223> OTHER INFORMATION: Description of Artificial Sequence:nptII coding region translationally fused to coat protein coding sequence and preceded by STNV-2 leader

<400> SEQUENCE: 38
gagctctaga ggtctcgagt aaagacagga aactttaccg actatcagaa tgacaaaacg 60
tcaaagcaaa caatcaaacc gcaagagcgt tgcatcacag gtgcgtagta ttgttgagtc 120
aatggctgag cagaagcgat ttgcttttct tacgaacacc aacacagtca ctacagcagg 180
taccgtgatc cggccaagct tggatggatt gcacgcaggt tctccggccg cttgggtgga 240
gaggctattc ggctatgact gggcacaaca gacaatcggc tgctctgatg ccgccgtgtt 300
ccggctgtca gcgcaggggc gcccggttct ttttgtcaag accgacctgt ccggtgccct 360
gaatgaactg caggacgagg cagcgcggct atcgtggctg gccacgacgg gcgttccttg 420
cgcagctgtg ctcgacgttg tcactgaagc gggaagggac tggctgctat tgggcgaagt 480
gccggggcag gatctcctgt catctcacct tgctcctgcc gagaaagtat ccatcatggc 540
tgatgcaatg cggcggctgc atacgcttga tccggctacc tgcccattcg accaccaagc 600
gaaacatcgc atcgagcgag cacgtactcg gatggaagcc ggtcttgtcg atcaggatga 660
tctggacgaa gagcatcagg ggctcgcgcc agccgaactg ttcgccaggc tcaaggcgcg 720
catgcccgac ggcgaggatc tcgtcgtgac ccatggcgat gcctgcttgc cgaatatcat 780
ggtggaaaat ggccgctttt ctggattcat cgactgtggc cggctgggtg tggcggaccg 840
ctatcaggac atagcgttgg ctacccgtga tattgctgaa gagcttggcg gcgaatgggc 900
tgaccgcttc ctcgtgcttt acggtatcgc cgctcccgat tcgcagcgca tcgccttcta 960
tcgccttctt gacgagttct tctgagcggg actctggggt tcg 1003

<210> SEQ ID NO 39
<211> LENGTH: 818
<212> TYPE: DNA
<213> ORGANISM: Artificial Sequence
<220> FEATURE:
<223> OTHER INFORMATION: coding region = 1 through 798
<220> FEATURE:
<223> OTHER INFORMATION: Description of Artificial Sequence:nptII coding region flanked by suitable restriction sites

<400> SEQUENCE: 39
atgaattcca gcttggatgg attgcacgca ggttctccgg ccgcttgggt ggagaggcta 60
ttcggctatg actgggcaca acagacaatc ggctgctctg atgccgccgt gttccggctg 120
tcagcgcagg ggcgcccggt tctttttgtc aagaccgacc tgtccggtgc cctgaatgaa 180
ctgcaggacg aggcagcgcg gctatcgtgg ctggccacga cgggcgttcc ttgcgcagct 240
gtgctcgacg ttgtcactga agcgggaagg gactggctgc tattgggcga agtgccgggg 300
caggatctcc tgtcatctca ccttgctcct gccgagaaag tatccatcat ggctgatgca 360
atgcggcggc tgcatacgct tgatccggct acctgcccat tcgaccacca agcgaaacat 420
cgcatcgagc gagcacgtac tcggatggaa gccggtcttg tcgatcagga tgatctggac 480
gaagagcatc aggggctcgc gccagccgaa ctgttcgcca ggctcaaggc gcgcatgccc 540
gacggcgagg atctcgtcgt gacccatggc gatgcctgct tgccgaatat catggtggaa 600
aatggccgct tttctggatt catcgactgt ggccggctgg gtgtggcgga ccgctatcag 660
gacatagcgt tggctacccg tgatattgct gaagagcttg gcggcgaatg ggctgaccgc 720
ttcctcgtgc tttacggtat cgccgctccc gattcgcagc gcatcgcctt ctatcgcctt 780
cttgacgagt tcttctgagc gggactctgg ggttcgaa 818

<210> SEQ ID NO 40
<211> LENGTH: 98
<212> TYPE: DNA
<213> ORGANISM: Artificial Sequence
<220> FEATURE:
<223> OTHER INFORMATION: Description of Artificial Sequence:5' UTR of TNV-AC36

<400> SEQUENCE: 40
gaccttacca aactttcaaa gaagataatt ctaagataca gtacattaca atcggcggag 60
cactactaca aaagtgtcaa caaattaata atgcctaa 98

<210> SEQ ID NO 41
<211> LENGTH: 308
<212> TYPE: DNA
<213> ORGANISM: Artificial Sequence
<220> FEATURE:
<223> OTHER INFORMATION: Location 19..49; note = "pseudoknot 1"
<220> FEATURE:
<223> OTHER INFORMATION: Location 63..92; note = "hairpin 1"
<220> FEATURE:

-continued

```
<223> OTHER INFORMATION: Location 102..227; note = "hairpin 2"
<220> FEATURE:
<223> OTHER INFORMATION: Location 230..272; note = "hairpin 3"
<220> FEATURE:
<223> OTHER INFORMATION: Location 288..303; note = "hairpin 4"
<220> FEATURE:
<223> OTHER INFORMATION: Description of Artificial Sequence:3' UTR of
      TNV-AC36

<400> SEQUENCE: 41

tagtcgcttt catagatccg tcttcccaga gacgttaaga agaaactgga gaaaaatatt     60

agtttaggaa cttgggcttg acaaacccaa gtggcatctc ttacgtggtt aatcacactg    120

catgttgacg aataggatgg atcctgggaa acaggtttaa cgggctctct gtggtggagg    180

gccgacgcat cacctatttg tgctccagca gtggttgtca tcacgtgtcc tgacatggct    240

ccatgcgaca gcatgggggg gtccagagtc agtcccctct ttatttacct aggttttcct    300

aggaaccc                                                             308
```